United States Patent [19]

Reese

[11] Patent Number: 5,708,161
[45] Date of Patent: Jan. 13, 1998

[54] NUCLEOSIDE PHOSPHOROTHIOATE DERIVATIVES, SYNTHESIS AND USE THEREOF

[75] Inventor: Colin Bernard Reese, Loindon, United Kingdom

[73] Assignee: King's College London, London, United Kingdom

[21] Appl. No.: 590,280

[22] Filed: Jan. 23, 1996

[30] Foreign Application Priority Data

Jan. 25, 1995 [GB] United Kingdom .................. 95 01465

[51] Int. Cl.$^6$ ............................. C07H 1/02; C07H 21/04
[52] U.S. Cl. ................................ 536/25.33; 536/25.3
[58] Field of Search .............................. 536/25.3, 25.33

[56] References Cited

FOREIGN PATENT DOCUMENTS 9313118    7/1993    WIPO .
9532980   12/1995    WIPO .

OTHER PUBLICATIONS

Harpp and Beck, "The Preparation of N–(Alkyl and Aryl-sulfinyl)–Phthalimides. A New Class of Sulfinyl–Transfer Reagents," *Tetrahedron Letters*, 52: 5313–5316 (Dec. 1972).

Rao et al., "Dibenzoyl Tetrasulphide –A Rapid Sulphur Transfer Agent in the Synthesis of Phosphorothioate Analogues of Oligonucleotides," *Tetrahedron Letters*, 33(33): 4839–4842 (Aug. 11, 1992).

Reese et al., "Action of Toluene–p–thiol and Triethylamine on Fully Protected Thymidylyl–(3'→5')–thymidine. Possible Occurrence of Thiolate Ion–promoted Internucleotide Cleavage in the Synthesis of Oligonucleotides by the Phosphotriester Approach," *J. Chem. Soc. Perkin Trans., I*: 2451–2455 (1981).

Schaller et al., "Studies on Polynucleotides. XXIV The Stepwise Synthesis of Specific Deoxyribopolynucleotides (4). Protected Derivatives of Deoxyribonucleosides and New Syntheses of Deoxyribonucleoside–3' Phosphates," *J. Am. Chem. Soc.*, 85: 3821–3827 (1963).

(List continued on next page.)

*Primary Examiner*—Gary L. Kunz
*Attorney, Agent, or Firm*—Leona L. Lauder

[57] ABSTRACT

Inter alia, a process for the production of a nucleoside phosphorothioate derivative corresponding to the following general formula (I):

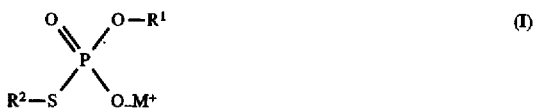

characterized in that it comprises reacting a salt of a nucleoside H-phosphonate corresponding to the following general formula (II):

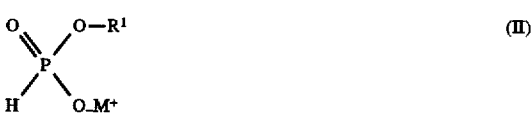

with a thiol transfer agent corresponding to the following general formula (III):

$$R^2-S-X \qquad (III)$$

in the presence of a silylating agent and a base in a suitable solvent; and working-up the reaction mixture to isolate the desired product and change the counter-cation as desired; wherein $M^+$ represents a suitable counter-cation;

$R^1$ represents an appropriate nucleoside or nucleoside analogue;

$R^2$ represents a desired protecting group, which may ultimately be removable by cleavage of its bond to the sulfur atom; and X represents a leaving group, is disclosed.

25 Claims, 1 Drawing Sheet

OTHER PUBLICATIONS

Sinha, N. D., "Large-Scale Oligonucleotide Synthesis Using the Solid-Phase Approach," (Chapter 18) *Methods in Molecular Biology, vol. 20: Protocols for Oligonucleotides and Analogs*, Ed. S. Agrawal, Humana Press, Inc. Totowa, NJ, pp. 437–463 (1993).

Stec and Wilk, "Stereocontrolled Synthesis of Oligo(nucleoside phosphorothioate)s," *Angew. Chem. Int. Ed. Engl.*, 33:709–722 (1994).

Zhao Zhengyun, "Studies in the Chemistry of the Thio-Analogues of Nucleotides and Oligonucleotides," Thesis, University of London, King's College, pp. 181–182, (Jul. 1993).

Zon and Stec, "Phosphorothioate oligonucleotides," (Chapter 4) *Oligonucleotides and Analogues –A Practical Approach*, Ed. F. Eckstein, IRL Press, Oxford, pp. 87–108 (1991).

Zon, G., "Oligonucleoside Phosphorothioates," (Chapter 8) *Methods in Molecular Biology, vol. 20: Protocols for Oligonucleotides and Analogs*, Ed. S. Agrawal, Humana Press, Inc., Totowa, NJ, pp. 165–189 (1993).

Bauer and Welsh, "Addition of Thiourea to Acrylonitrile and Acrylamides," *J. Org. Chem.*, 26: 1443–1445 (May 1961).

Beaucage, S. L., "Oligodeoxyribonucleotides Synthesis: Phosphoramidite Approach," *Methods in Molecular Biology, vol. 20: Protocols for Oligonucleotides and Analogs*, Ed. S. Agrawal, Humana Press, Inc., Totowa, NJ, pp. 33–61 (1993).

Behforouz and Kerwood, "Alkyl and Aryl Sulfenimides," *J. Org. Chem.*, 34(1): 51–55 (Jan. 1969).

Benseler and McLaughlin, "An Improved Procedure for the Protection of 2'-Deoxyguanosine," *Synthesis*: 45–46 (Jan. 1986).

Burgers and Eckstein, "Diastereomers of 5'-O-Adenosyl 3'-O-Uridyl Phosphorothioate: Chemical Synthesis and Enzymatic Properties," *Biochemistry*, 18(4): 592–596 (1979).

Chattopadhyaya and Reese, "The 9-Phenylxanthen-9-yl Protecting Group," *J.C.S. Chem. Comm.*: 639–640 (1978).

Christodoulou and Reese, "Dealkylation of Nucleoside Arylmethyl 2-Chlorophenyl Phosphates: the 2,4-Dinitrobenzyl Protecting Group," *Tetrahedron Letters*, 24(9): 951–954 (1983).

Cohn and Friedländer, "UeberO-p-Dinitrobenzaldehyd," *Ber.*, 35: 1265–1267 (1902).

Cosstick and Williams, "An approach to the stereoselective synthesis of Sp-dinucleoside phosphorothioates using phosphotriester chemistry," *Nucleic Acids Research*, 15(23): 9921–9932 (1987).

Dreef et al., "A Convenient Approach Towards the Conversion of H-Phosphonate and H-Phosphonothioate Diesters into Phosphoro–(di)thioate Derivatives," *Synlett (Letters)*: 481–483 (Aug. 1990).

Froehler et al., "Synthesis of DNA via deoxynucleoside H-phosphonate intermediates," *Nucleic Acid Research*, 14(13): 5399–5407 (1986).

Ghosh et al., "Evaluation of some properties of a phosphorodithioate oligodeoxyribonucleotide for antisense application," *Nucleic Acids Research*, 21(24): 5761–5766 (1993).

Horn, W. J., "Researches on Pyrimidines. XCI. Alkylation of 2-Mercapto-Pyrimidines," *J. Am. Chem. Soc*, 43: 2603–2611 (1921).

Horwitz et al., "Nucleosides. II. 5'-O-Mesylthymidine and 3'-O-Mesylthymidine," *J. Org. Chem.*, 27: 3300–3302 (1962).

Jones et al., "Synthesis of the 3'-Terminal Decaribonucleoside Nonaphosphate of Yeast Alanine Transfer Ribonucleic Acid," *Tetrahedron*, 36: 3075–3085 (1980).

Kamimura et al., "Synthesis of a Dodecaribonucleotide, GUAUCAAUAAUG, by Use of 'Fully' Protected Ribonucleotide Building Blocks," *J. Am. Chem. Soc.*, 106(16): 4552–4557 (1984).

Kemal et al., "Use of 2,5-Dichlorophenyl Phosphorodichloridothioate in the Synthesis of Diasteroisomeric Dinucleoside Phosphorothioates," *J. Chem. Soc. Chem. Communo.*: 591–593 (1983).

Lesnikowski and Jaworska, "Studies on Stereospecific Formation of P-Chiral Internucleotide Linkage. Synthesis of (Rp,Rp)–and (Sp,Sp)–Thymidyly(3',5')Thymidyly(3', 5')Thymidine Di(O,O–phosphorothioate) Using 2-Nitrobenzyl Group as New S-Protection," *Tetrahedron Letters*, 30(29): 3821–3824 (1989).

Miller, B., "Ease of Displacement of Thiol and Oxide Anions from Methyl Groups: Carbon Basicities of Anions of Oxygen and Sulphur," *Proc. Chem. Soc.*: 303 (Sep. 1962).

Müller and Roth, "A New Synthesis of Thiophosphoric Acid Esters with a C–S–P Bond," *Tetrahedron Letters*, 31(4): 501–502 (1990).

Nielsen et al., "Synthesis and Characterization of Dinucleoside Phosphorodithioates," *Tetrahedron Letters*, 29(24): 2911–2914 (1988).

Pant and Noltes, "The Reaction of Lead Bisthiolates with N-Halosuccinimides," *Inorg. Nucl. Chem. Letters*, 7(1): 63–66 (1971).

Porritt and Reese, "Use of the 2,4-Dinitrobenzyl Protecting Group in the Synthesis of Phosphorodithioate Analogues of Oligodeoxyribonucleotides," *Tetrahedron Letters*, 31(9): 1319–1322 (1990).

Rao and Reese, "Synthesis of cyclic oligodeosyribonucleotides via the 'filtration' approach," *Nucleic Acids Research*, 17(20): 8221–8239 (1989).

Reese, C. B., "The Chemical Synthesis of Oligo–and Poly-–Nucleotides by the Phosphotriester Approach," *Tetrahedron (Report No. 56)*, 34: 3143–3179 (1978).

Reese and Skone, "The protection of Thymine and Guanine Residues in Oligodeoxyribonucleotide Synthesis," *J. Chem. Soc. Perkin Trans., I*: 1263–1271 (1984).

Reese and Pei-Zhuo, "Phosphotriester Approach to the Synthesis of Oligonucleotides: A Reappraisal," *J. Chem. Soc. Perkin Trans., I*: 2291–2301 (1993).

NUCLEOSIDE PHOSPHOROTHIOATE DERIVATIVES, SYNTHESIS AND USE THEREOF

This invention relates to nucleoside phosphorothioate derivatives, synthesis and use thereof.

More particularly, one embodiment of the present invention relates to the improved production of nucleoside phosphorothioate derivatives corresponding to the following general formula (I):

wherein $M^+$ represents a suitable counter-cation, such as $Et_3NH^+$;

$R^1$ represents an appropriate nucleoside or nucleoside analogue; and $R^2$ represents a desired protecting group, which may ultimately be removable by cleavage of its bond to the sulfur atom. The nucleoside or nucleoside analogue $R^1$ includes a suitably protected sugar and/or base residue as appropriate. $R^1$ may be derived from a natural 2'-deoxyribo- or ribo-nucleoside or an analogue thereof. The protecting group $R^2$ may be alkyl, such as methyl, substituted alkyl, such as 2-cyanoethyl, aralkyl, such as benzyl, which may be mono- or di-nitro-substituted, alkenyl, such as allyl, or substituted alkenyl. The group $R^2$ need not be removed in the present process. For example, such nucleoside phosphorothioate derivatives (I) could also be used in the synthesis of per-S-alkyl, -aralkyl and -alkenyl esters of oligonucleotide phosphorothioates that would have enhanced lipophilicity, thereby facilitating cellular uptake.

An appropriate salt of a nucleoside H-phosphonate corresponding to the following general formula (II):

is reacted with a suitable thiol transfer agent corresponding to the following general formula (III):

wherein X represents a leaving group, such as the conjugate base of succinimide or phthalimide, either of which may be substituted; in the presence of a silylating agent, such as chlorotrimethylsilane, and a base, such as triethylamine or 4-methylmorpholine, in a suitable solvent, such as dichloromethane. The reaction mixture is then worked-up to isolate the desired products and the counter-cation changed as desired. For example, the products may be poured into aqueous triethylammonium hydrogen carbonate and the resulting mixture extracted with dichloromethane.

Particularly preferred thiol transfer agents (III) include N-(2-cyanoethylmercapto)phthalimide and the corresponding succinimide compound. A further embodiment of the present invention is directed accordingly.

The nucleoside phosphorothioate derivatives which may be prepared by the present advantageous process are particularly suitable for use as building blocks for the large-scale production of phosphorothioate analogues of oligonucleotides by the phosphotriester approach, preferably in solution. Another embodiment of the present invention is directed accordingly.

Having indicated some aspects of the present invention in general terms, such will now be illustrated in more detail.

The potential importance of antisense chemotherapy (see, for example, *Oligodeoxynucleotides: Antisense Inhibitors of Gene Expression*, Ed. Cohen, J. S., Macmillan, London, 1989) has stimulated organic chemists to undertake the synthesis of a variety of oligonucleotide analogues and especially those analogues in which the internucleotide linkages and sugar residues are modified. Perhaps the most widely investigated analogues in this context are oligodeoxyribonucleotide phosphorothioates, (see, for example, the above mentioned reference; Zon G., and Stec W. J., *Oligonucleotides and Analogues—A Practical Approach*, Ed. Eckstein, F., IRL Press, Oxford, 87–108, 1991; and Zon G., *Methods in Molecular Biology*, Vol 20, *Protocols for Oligonucleotides and Analogs*, Ed. Agrawal, S., Humana, Totowa, 165–189, 1993), e.g. 1:

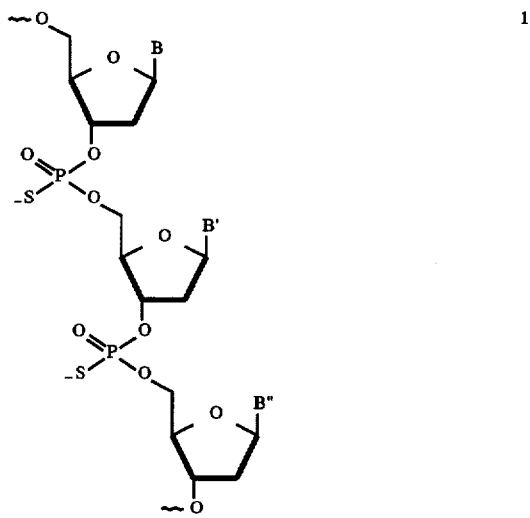

Indeed, it is believed, (see, for example, Stec, W. J., and Wilk, A., *Angew. Chem. Int. Ed. Engl.*, 33, 709, 1994), that several such sequences are presently undergoing clinical trials. By far the most convenient method of preparing small (say, of the order of $10^{-6}$ mol) quantities of the latter analogues is by automated solid phase synthesis using standard phosphoramidite building blocks, (see, for example, Beaucage, S. L., *Methods in Molecular Biology*, Vol 20, *Protocols for Oligonucleotides and Analogs*, Ed. Agrawal, S., Humana, Totowa, 33–61, 1993), and replacing the normal iodine-promoted oxidation by a sulfur-transfer step, (see, for example, Zon and Stec, and Zon, loc cit). Although this approach does not lead to control of the stereochemistry of the chiral phosphorothioate internucleotide linkages, the synthetic analogues appear to have satisfactory hybridisation properties, (see, for example, Ghosh, M. K., et at, Nucleic Acids Res., 21, 5761, 1993).

It would appear from the literature, (see, for example, Zon, loc cit), that attempts to address the potential need for much larger (say, of the order of $10^{-3}$ mol or possibly considerably more) quantifies of specific oligodeoxyribonucleotide phosphorothioates have mainly involved the scale-up of phosphoramidite-based solid phase synthesis. The particular advantages of solid phase synthesis, at least on the $10^{-6}$ molar scale, are that it may readily be automated, coupling reactions are generally very fast and efficient and that it is very flexible in that, as only one nucleotide residue is added at a time, the target sequence may very easily be changed. However, when the large-scale synthesis of a specific oligonucleotide sequence is to be undertaken, there will be a number of drawbacks to the use of solid phase synthesis. For example, a relatively large excess of phosphoramidite building block is generally required, (see, for example, Sinha, N. D., *Methods in Molecular Biology*, Vol 20, *Protocols for Oligonucleotides and Analogs*, Ed. Agrawal, S., Humana, Totowa, 437–463, 1993), in each coupling step and coupling efficiencies may well fall as the scale increases. Furthermore, the addition of more than one nucleotide in each coupling step would probably be costly and perhaps also inconvenient. For such reasons, the phosphotriester approach in solution, (see, for example, Reese, C. B., *Tetrahedron*, 34, 3143, 1978), might prove to be a superior method for the synthesis of large quantities of specific oligonucleotides and analogues thereof. The most obvious merits of the phosphotriester approach are (i) that scale-up should not present a problem, (ii) that only a relatively small (say, 25–50%) excess of building block is likely to be required, (see, for example, Reese, C. B., and Zhang Pei-Zhuo, *J. Chem. Soc., Perkin Trans* 1, 2291, 1993), in each coupling step, and (iii) that the addition of two or more nucleotide residues at a time (i.e. block synthesis) would be a routine operation. It was decided to investigate the feasibility of the large-scale synthesis of oligonucleotide phosphorothioates by the phosphotriester approach in solution. As indicated above, the present invention may be regarded as being particularly concerned with the choice of a protecting group for the internucleotide linkages and the preparation of suitable monomeric building blocks.

A general strategy for the synthesis of oligodeoxyribonucleotide phosphorothioates by the phosphotriester approach is indicated in outline in Scheme I:

Scheme 1

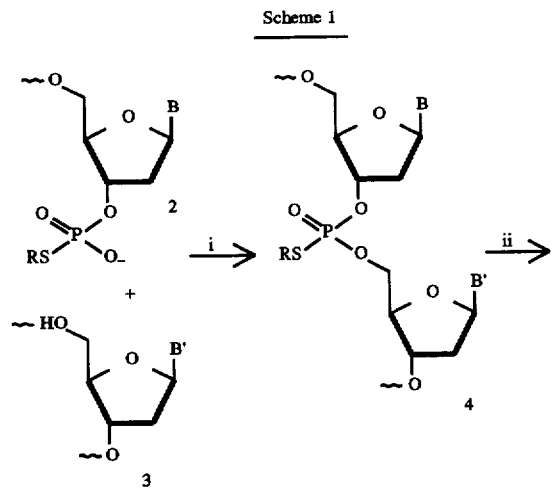

-continued
Scheme 1

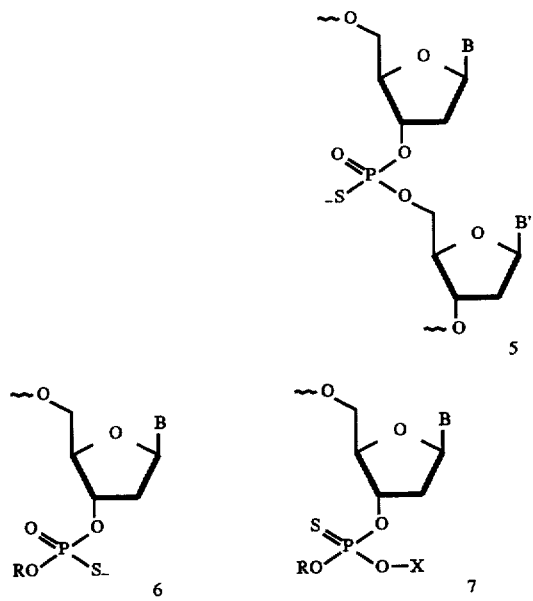

The key step (step i) involves coupling (effected by a condensing agent; see below) between a protected monomer or oligomer 2 terminating in an S-protected 3'-phosphorothioate diester and a protected monomer or oligomer 3 terminating in a 5'-hydroxy function to give the fully-protected phosphorothioate triester 4. It is essential that the 3'-phosphorothioate 2 should be protected on sulfur. If 2 were replaced by the corresponding O-protected phosphorothioate 6 and activation by the condensing agent occurred on sulfur, loss of sulfur would occur during the coupling reaction. However, even if activation of 6 occurred entirely on oxygen (to give an intermediate such as 7 containing a P—S double bond), the ensuing phosphorylation reaction might proceed relatively slowly and then be accompanied by the concomitant direct attack of the condensing agent on the 5'-hydroxy function of 3, thereby leading to a diminished yield of the required product 4.

A crucial decision to be made at the outset is the choice of the protecting group R (Scheme 1) for the internucleotide linkages. For the present purposes, it was decided that R must fulfil at least three main criteria. Firsfly, it must be such that pure phosphodiester intermediates 2 are readily accessible in high yields. Secondly, it must remain completely intact during the assembly of the required fully-protected oligonucleotide sequences 4. Thirdly, it must be easily removable [Scheme 1, step ii] in such a way that only unprotected oligonucleotide analogues with exclusively phosphorothioate internucleotide linkages are obtained. In order to meet this last criterion, the protecting group R must clearly be removed by cleavage of the R—S rather than the S-phosphoryl bond.

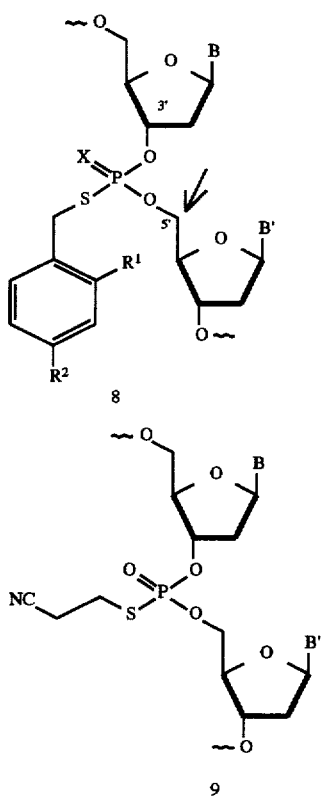

a: X=S, R¹R²=Cl b: X=S, R¹=R²=NO₂ c: X=O, R¹=NO₂, R²=H d: X=O, R¹=H, R²=NO₂

Recently, substituted benzyl protecting groups, such as 2,4-dichlorobenzyl, (see, for example, Nielsen, J., et al, Tet. Lett., 29, 2911, 1988), (as in 8a) and 2,4-dinitrobenzyl, (see, for example, Porritt, G. M., and Reese, C. B., Tet. Lett., 31, 1319, 1990), (as in 8b), have been used in the preparation of phosphorodithioate analogues of oligonucleotides. Such protecting groups may be removed by the nucleophilic attack of thiolate ions (e.g. the conjugate bases of thiophenol, (see, for example, Nielsen et al, loc cit), and p-thiocresol, (see, for example, Porritt and Reese, loc. cit) on the benzylic CH₂ groups. As carbon-oxygen bonds are much more readily cleaved by this process than carbon-sulfur bonds, (see, for example, Miller, B., Proc. Chem. Soc., 303, 1962), there is a real danger of concomitant nucleophilic attack occurring, (see, for example, Reese, C. B., et al, J. Chem. Soc., Perkin Trans. 1, 2451, 1981), on the 5'-carbon atoms adjacent to the internucleotide linkages (as indicated by the arrow in 8), resulting in internucleotide cleavage. In order to avoid this most undesirable side-reaction, (see, for example, Reese, et al, loc cit), it is essential that a particularly labile benzyl group (such as 2,4-dinitrobenzyl as in 8b) should be used. 2-Nitrobenzyl, (see, for example, Lesnikowski, Z. J., and Iaworska, M. M., Tet. Lett., 30, 3821, 1989), (as in 8c) and 2-cyanoethyl, (see, for example, Burgers, P. M. J., and Eckstein, F., Biochemistry, 18, 592, 1979; and Cosstick, R., and Williams, D. M., Nucleic Acids Res., 15, 9921, 1987), (as in 9) have been suggested as S-protecting groups in the synthesis of phosphorothioate analogues of oligonucleotides. The latter (i.e. 2-cyanoethyl) protecting group may be removed by a base-catalyzed β-elimination process. Largely with a consideration of the ease of unblocking the internucleotide linkages (Scheme 1, step ii) in mind, this investigation of possible protecting groups (R, Scheme 1) has concentrated on 4-nitrobenzyl (as in 8d) which seemed likely, (see, for example, Christodoulou, C., and Reese,. C. B., Tel. Lett., 24, 951, 1983), to be more readily removable by thiolate ion attack than 2-nitrobenzyl (as in 8c), 2,4-dinitrobenzyl (as in 8, X=O, R¹=R²=NO₂) and 2-cyanoethyl (as in 9).

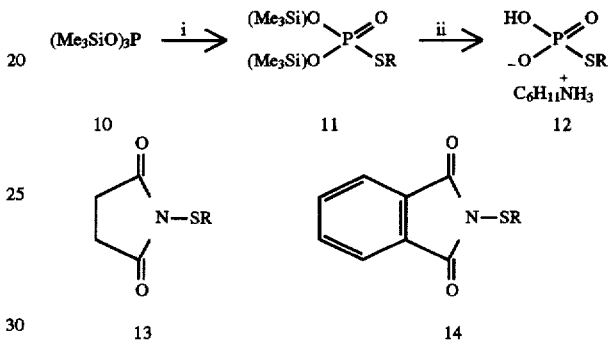

Scheme 2 Reagents and conditions: i, 13 (R=alkyl or aryl) or 14 (R=alkyl or aryl); ii, a, hydrolysis, b, cyclohexylamine.

It has recently been reported, (see, for example, Müller, C. E., and Roth, H. J., Tet. Lett., 31,501, 199.0), that tris (trimethylsilyl) phosphite 10 reacted rapidly with N-(alkylmercapto)- and N-(arylmercapto)-succinimides 13 to give (Scheme 2) the corresponding bis(trimethylsilyl) S-alkyl and S-aryl phosphorothioates 11, respectively, and that the latter products readily underwent hydrolysis to give S-alkyl and S-aryl phosphorothioates 12; it was also reported that, (see, for example, Müller and Roth, loc cit), N-(alkylmercapto)- and N-(arylmercapto)-phthalimides 14 could be used instead of the corresponding succinimide derivatives 13. It was then shown, (see, for example Dreef, C. E., et al, Synlett., 481, 1990), that dinucleoside H-phosphonates may be converted into S-benzyl and S-phenyl esters of dinucleoside phosphorothioates by treatment with N-(benzylmercapto)- and N-(phenylmercapto)-succinimides (13, R=PhCH₂ and 13, R=Ph, respectively) in the presence of di-isopropylethylamine. It was decided to attempt to prepare the monomeric S-alkyl phosphorothioate building blocks that are required (see below) for the synthesis of phosphorothioate analogues of oligonucleotides by the phosphotriester approach in solution, by using a modification of the above method, (see, for example, Müller and Roth, loc cit). There were therefore needed N-(alkylmercapto)-succinimide or -phthalimide derivatives (13 or 14) or equivalents thereof derived from 4-nitrobenzyl, 2,4-dinitrobenzyl and 2-cyanoethyl mercaptans (17a, 17b and 20, respectively).

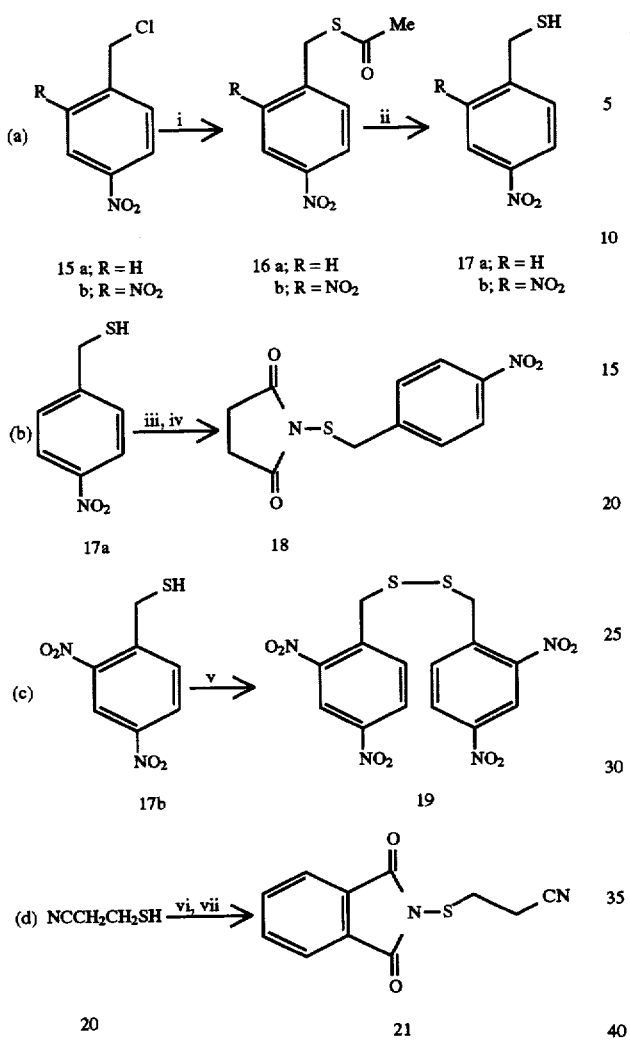

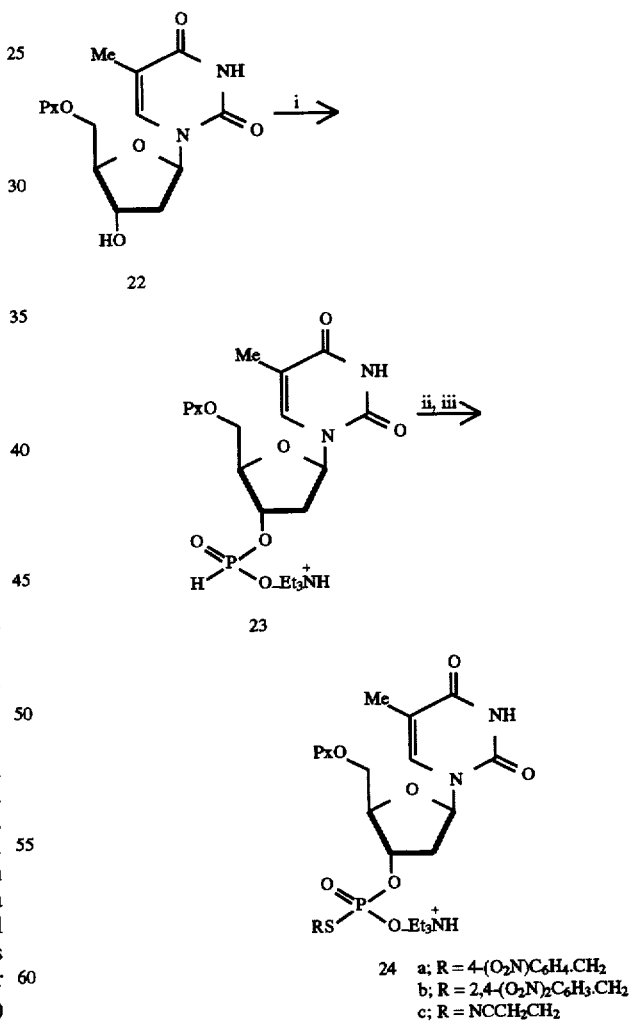

24 a; R = 4-(O₂N)C₆H₄.CH₂
b; R = 2,4-(O₂N)₂C₆H₃.CH₂
c; R = NCCH₂CH₂

Scheme 3 Reagents and conditions: i, CH₃C(O)SH, C₅H₅N, THF; ii, H₂SO₄—H₂O (1:1 v/v), reflux; iii, Pb(OAc)₂, MeOH, RT; iv, NBS, C₆H₆, 50° C., 14 h; v, I₂, CH₂Cl₂, RT, 16 h; vi, Cl₂, CH₂Cl₂, 0° C., 20 min; vii, phthalimide, Et₃N, hexane, 0° C. to RT.

The two step procedure for the preparation of 4-nitrobenzyl, (see, for example, Horn, W. J., J. Am. Chem. Soc., 43, 2603, 1921), and 2,4-dinitrobenzyl, (see, for example, Zhao Zhengyun, Ph.D. Thesis, London University, 181–182, 1993), mercaptans (17a and 17b, respectively) is indicated in outline in Scheme 3(a). Thus, when 4-nitrobenzyl chloride 15a was treated with an excess both of thioacetic acid and pyridine in THF solution at 50° C., 4-nitrobenzyl thioacetate 16a was obtained in 77% yield. When the latter compound 16a was heated, under reflux, in sulfuric acid—water (1:1 v/v), 4-nitrobenzyl mercaptan 17a was obtained in almost quantitative yield. 2,4-dinitrobenzyl mercaptan, (see, for example, Zhao, loc cit), 17b was similarly prepared from 2,4-dinitrobenzyl chloride, (see, for example, Cohn, P., and Friedländer, P., Ber., 35, 1265, 1902) 15b in 73% overall yield. N-(4-nitrobenzylmercapto) succinimide 18 was prepared [Scheme 3(b) and Experimental below] in 65 % yield by heating a suspension of the lead(II) salt, (see, for example, Pant, B.C., and Noltes, J. G., Inorg. Nucl. Chem. Lett., 7, 63, 1971), of the mercaptan 17a with N-bromosuccinimide (NBS) in benzene. Preliminary attempts to convert 2,4-dinitrobenzyl mercaptan 17b into the corresponding succinimide and phthalimide derivatives (13 and 14, R=2,4-(O₂N)₂C₆H₃) were unsuccessful. However, di-(2,4-dinitrobenzyl) disulfide 19, (see, for example, Zhao, loc cit), which was easily prepared in good yield by the iodine-promoted oxidation [Scheme 3(c) and Experimental below] of the mercaptan 17b, proved (see below) to be an equally effective reagent for the required purpose. Finally, 2-cyanoethyl mercaptan 20, (see, for example, Bauer, L., and Welsh, T. L., J. Org. Chem., 26, 1443, 1961) was converted (see, for example, Behforouz, M., and Kerwood, J. E., J. Org. Chem., 34, 51, 1969), [Scheme 3(d) and Experimental below] via a putative intermediate sulfenyl chloride into N-(2-cyanoethylmercapto)phthalimide 21 which was isolated without chromatography as a crystalline solid in 58% yield.

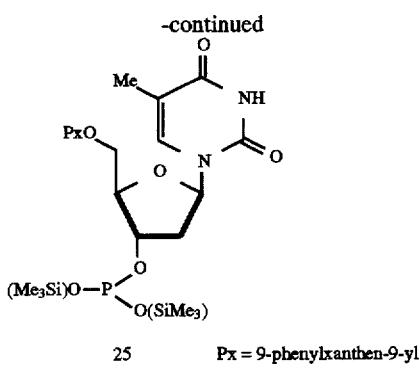

25  Px = 9-phenylxanthen-9-yl

Scheme 4 Reagents and conditions: i, a, PCl$_3$, 1,2,4-1H-triazole, Et$_3$N, THF, −35° C., b, Et$_3$N, H$_2$O, RT; ii, for 24a: 18, Me$_3$SiCl, Et$_3$N, CH$_2$Cl$_2$, RT, for 24b: 19, Me$_3$SiCl,4-methylmorpholine, CH$_2$Cl$_2$, RT, for 24c: 21, Me$_3$SiCl, 4-methylmoxpholine, CH$_2$Cl$_2$, RT; iii, aq. Et NH$^+$ HCO$_3$—.

It was decided in the first instance to convert 5'-O-(9-phenylxanthen-9-yl)thymidine 22, (see, for example, Chattopadhyaya, J. B., and Reese, C. B., J. Chem. Soc., Chem. Commun., 639, 1978), into the three S-alkyl phosphorothioate building blocks 24a, 24b and 24c (Scheme 4). The nucleoside derivative 22 was treated with a ca. fourfold excess of the reagent derived from-phosphorus trichloride and three molecular equivalents each of 1,2,4-1H-triazole and triethylamine in dry THF at −35° C., and the intermediate was hydrolysed with 0.5 mol dm$^{-3}$ aqueous triethylammonium bicarbonate to give, (see, for example, Froehler, B. C., et al, Nucleic Acids Res., 14, 5399, 1986) the triethylammonium salt of the 3'-(H-phosphonate) 23. Following chromatography of the products on silica gel, the latter material 23 was isolated as a colourless solid precipitate in almost quantitative yield (Table 1 below). When a dry solution of the latter H-phosphonate 23 and a slight excess of N-(4-nitrobenzylmercapto)succinimide 18 in dichloromethane was treated with ca. 4 molecular equivalents of chlorotrimethylsilane and ca. 6 molecular equivalents of triethylamine at room temperature for 2.5 h and the products worked up with aqueous triethylammonium bicarbonate buffer, the S-(4-nitrobenzyl) phosphorothioate 24 was obtained. Following chromatography of the products on silica gel, the latter compound 24 was isolated as a pale yellow precipitated solid in 86 % yield. It may be assumed that the reaction proceeds by the electrophilic attack of the succinimide derivative 18 on an intermediate bis-(trimethylsilyl)phosphite (such as 25). The S-(2,4-dinitrobenzyl)phosphorothioate24b was similarly prepared from the H-phosphonate 23, di-(2,4-dinitrobenzyl) disulfide 19, chlorotrimethylsilane and 4-methylmorpholine. As the benzylic protons of 2,4-dinitrobenzyl derivatives are likely to be particularly acidic, it is advisable to avoid the use of strong bases such as triethylamine. The desired product 24b was isolated as a precipitated solid in 67% yield. Finally, the S-(2-cyanoethyl) phosphorothioate 24c was prepared in the same way from the H-phosphonate 23, N-(2-cyanoethylmercapto)phthalimide 21, chlorotrimethylsilane and 4-methylmorpholine; it was isolated as a pure ($^{31}$P NMR and HPLC, see Table 1 below) precipitated solid in 92% yield. This represents a considerable improvement both in methodology and yield over a previously reported, (see, for example, Cosstick and Williams, loc cit) preparation of a related 2'-deoxynucleoside 3'-S-(2-cyanoethyl) phosphorothioate derivative.

The comparative suitabilities of the above three phosphorothioate S-alkyl protecting groups (R in Schemes 4 and 5) were examined by undertaking the synthesis of the simple dinucleoside phosphorothioate 30 (Scheme 5).

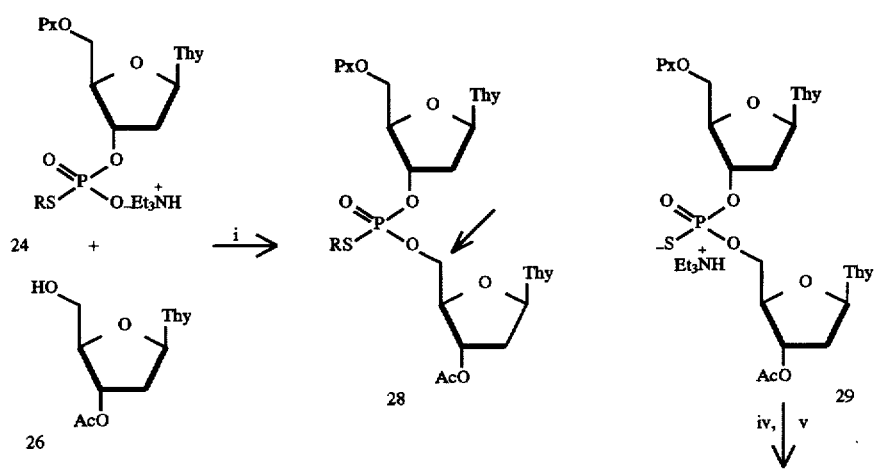

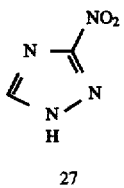
27

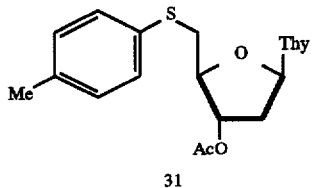
31

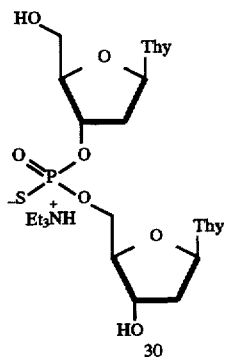
30

Px=9-phenylxanthen-9-yl; Thy=thymin-1-yl; a, R=4-(O$_2$N)C$_6$H$_4$.CH$_2$; b, R=2,4(O$_2$N)$_2$C$_6$H$_3$.CH$_2$; c, R=CH$_2$CH$_2$CN Scheme 5 Reagents and conditions; i, NT 27, mesitylene-2-sulfonyl chloride (MSCl), C$_5$H$_5$N, RT, 50 min; ii, 4-MeC$_6$H$_4$SH, Et$_3$N, MeCN, RT, 4.5 h; iii, t-BuNH$_2$, C$_5$H$_5$N, RT, 100 min; iv, conc. aq. NH$_3$ (d 0.88), RT, 40 min; v, H$_2$O-AcOH (96:4, v/v), RT, 4 h.

First, the triethylammonium salt of 5'-O-(9-phenylxanthen-9-yl)thymidine 3'-phosphorothioate S-(4-nitrobenzyl) ester 24a and 3'-O-acetylthymidine 26, (see, for example, Horwitz, J. P., et al, J. Org. Chem., 27, 3300, 1962) were coupled together in the presence of mesitylene-2-sulfonyl chloride (MSCl) and 3-nitro-1,2,4-1H-triazole (NT) 27, (see, for example, Jones, S. S., et al, Tetrahedron, 36, 3075, 1980), in pyridine solution to give the fully-protected dinucleoside phosphate 28a. The latter material was isolated in 85% yield and characterized on the basis of NMR spectroscopic data (particularly $^{31}$P: $\delta_P$[(CD$_3$)$_2$SO] 27.47, 27.61). When an acetonitrile solution (ca. 0.02 mol dm$^{-3}$) of 28a was treated (see, for example, Christodoulou and Reese, loc cit) at room temperature with ca. 10 molecular equivalents of toluene-4-thiol and ca. 5 molecular equivalents of triethylamine, the main products (ca. 98%) were the diastereoisomeric partially-protected dinucleoside phosphorothioates 29 (see accompanying FIG. 1a, R$_t$ 10.73, 10.98 min). However, two other products (ca. 0.8 and 1.1%) which corresponded to 5'-O-(9-phenylxanthen-9-yl)thymidine 3'-phosphorothioate S-(4-nitrobenzyl ester) 24a (R$_t$ 11.87 min) and 3'-O-acetyl-5'-S-(4-methylphenyl)-5'-thiothymidine 31 (R$_t$ 12.05 min), respectively, were detected by HPLC (see accompanying FIG. 1a). It seems reasonable to conclude that the latter products resulted (see, for example, Reese, et al, loc cit), from the attack of toluene-4-thiolate ions at C-5' adjacent to the internucleotide linkage (as indicated by the arrow in 28). A level of ca. 2% cleavage per internucleotide linkage would be quite unacceptable if the synthesis of an oligonucleotide phosphorothioate even of moderate size were undertaken. It was therefore concluded that the 4-nitrobenzyl protecting group was unsuitable for the present purposes.

Unfortunately, the 2,4-dinitrobenzyl protecting group also proved to be unsuitable in that the NT 27/MSCl-promoted coupling reaction (Scheme 5) between 5'-O-(9-phenylxanthen-9-yl) thymidine 3'-phosphorothioate S-(2,4-dinitrob enzyl) ester 24b and 3'-O-acetylthymidine 26 did not lead to a detectable quahtity of the desired fully-protected dinucleoside phosphate 28b. Although the S-(2,4-dinitrobenzyl) group is known (see, for example, Porritt and Reese, loc cit), to be particularly susceptible to nucleophilic attack, this was still a surprising result. However, the NT 27/MSCl-promoted coupling reaction between 5'-O-(9-phenylxanthen-9-yl)thymidine 3'-phosphorothioate S-cyanoethyl ester 24e and 3'-O-acetylthymidine 26 proceeded satisfactorily to give the fully-protected dinucleoside phosphorothioate 28c. When the latter product 28c, which was isolated as a colourless precipitated solid ($\delta_P$[(CD$_3$)$_2$SO]27.62, 27.94) in 90% yield, was treated with a large excess of tert-butylamine (see, for example, Cosstick and Williams, loc cit), in pyridine solution at room temperature, it was cleanly unblocked to give the expected diastereoisomeric mixture of partially-protected dinucleoside phosphorothioates 29 ($\delta_P$[(CD$_3$)$_2$SO]55.96, 56.29) as the sole (see accompanying FIG. 1b for HPLC profile) nucleotide products. Further unblocking of this material 29 to give the fully-unprotected mixture of diastereoisomeric dinucleoside phosphorothioates 30 was readily effected (Scheme 5, steps iv and v) by treatment at room temperature first with concentrated aqueous ammonia and then with 4% acetic acid. The high purity of the unprotected dinucleoside phosphorothioate 30 obtained was established, (see, for example, Kemal, O, et al, J. Chem. Soc., Chem. Commun., 591, 1983), on the basis of NMR spectroscopic ($\delta_P$[(CD$_3$)$_2$SO] 56.00, 56.36) and HPLC data.

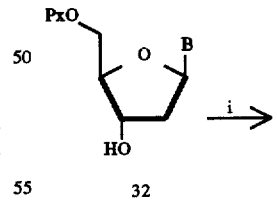
32

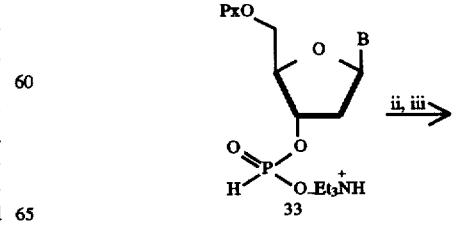
33

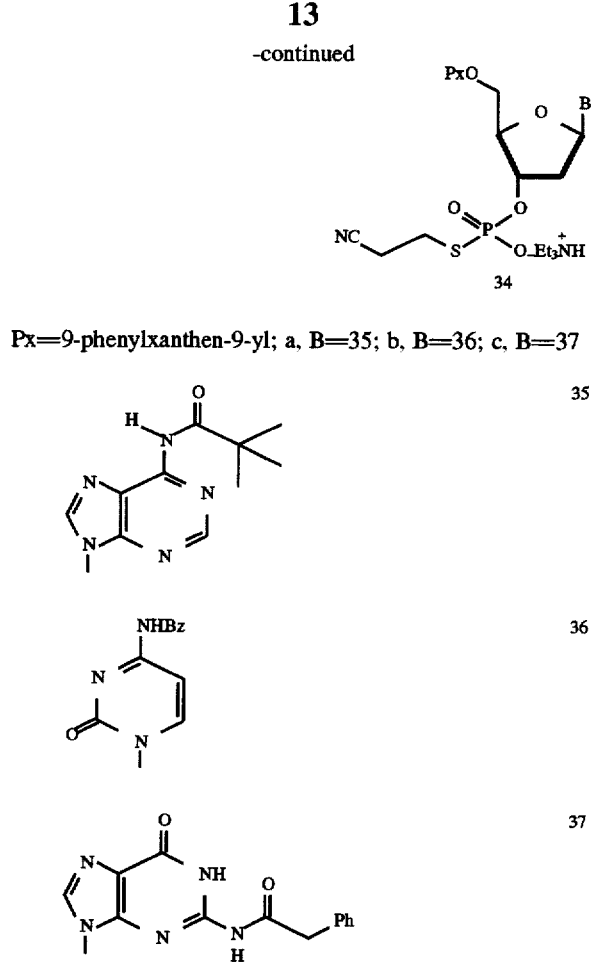

Px=9-phenylxanthen-9-yl; a, B=35; b, B=36; c, B=37

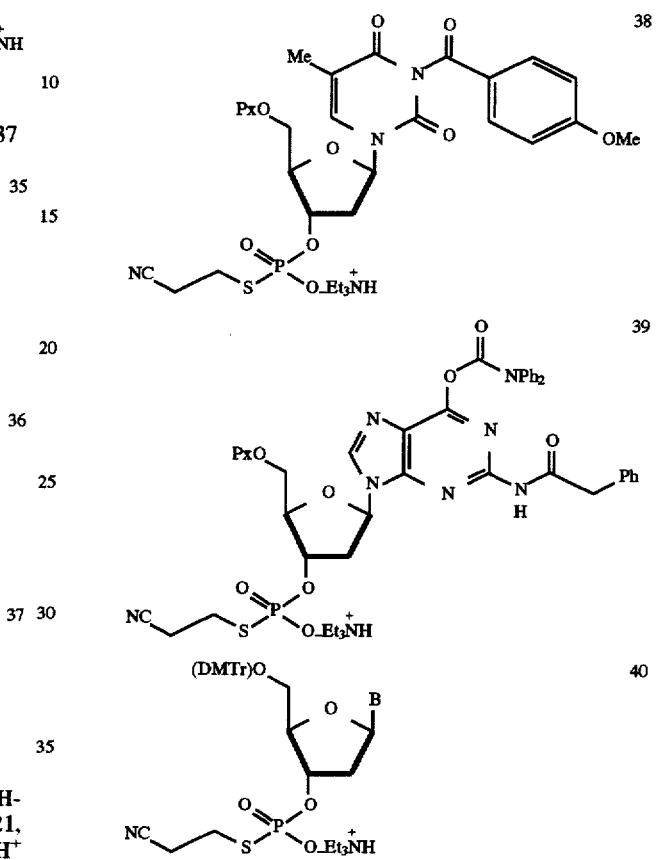

Scheme 6 Reagents and conditions: i, a, PCl$_3$, 1,2,4-1H-triazole, Et$_3$N, THF, −35° C., b, Et$_3$N, H$_2$O, RT; ii, 21, Me$_3$SiCl$_4$-methylmorpholine, CH$_2$Cl$_2$, RT; iii, aq. Et$_3$NH$^+$ HCO$_3$—

The above studies led to the conclusion that the 2-cyanoethyl group was likely to be suitable for the protection of the internucleotide linkages in the large-scale synthesis of oligodeoxyribonucleotide phosphorothioates by the phosphotriester approach in solution. The preparation of the required monomeric phosphorothioate building blocks derived from 2'-deoxyadenosine, 2'-deoxycytidine and 2'-deoxyguanosine was then undertaken. 5'-O-(9-phenylxanthen-9-yl)- 6-N-pivaloyl-2'-deoxyadenosine, (see, for example, Rao, M. V., and Reese, C. B., Nucleic Acids Res., 17, 8221, 1989), 32a was converted (Scheme 6) via an intermediate H-phosphonate 33a into the triethylammonium salt of its 3'-phosphorothioate S-(2-cyanoethyl) ester 34a by the same procedure as was used (Scheme 4) for the conversion of 5'-O-(9-phenylxanthen-9-yl)thymidine 22 into the corresponding monomeric building block 24c. It may be seen from Table 1 below that good yields both of the H-phosphonate 33a (entry no. 3) and the phosphorothioate 34a (entry no. 4) were obtained. Furthermore, the high purity of both products was established by HPLC and NMR spectroscopy (Table 1 below). In the same way, 4-N-benzoyl-5'-O-(9-phenylxanthen-9-yl)-2'-deoxycytidine, (see, for example, Chattopadhyaya and Reese, loc cit), 32b and 2-N-phenylacetyl-5'-O-(9-phenylxanthen-9-yl)-2'-deoxyguanosine, (see, for example, Benseler, F., and McLaughlin, L. W., Synthesis, 45, 1986) 32c were converted via intermediate 3'-(H-phosphonates) 33b and 33c (entries nos. 5 and 7, respectively) into the required 3'-phosphorothioate S-(2-cyanoethyl) esters 34b and 34c (entries nos. 6 and 8, respectively). All of the products were isolated as pure (HPLC, NMR) precipitated solids, and all of the yields except that of the protected 2'-deoxyguanosine 3'-(H-phosphonate) 33c (entry no. 7) were very satisfactory.

Px=9-phenylxanthen-9-yl; DMTr=di-(p-anisyl)phenylmethyl.

Earlier studies had suggested that, in the synthesis of oligonucleotides by the phosphotriester approach in solution, it is probably desirable, (see, for example, Reese, C. B., and Skone, P. A., J. Chem. Soc., Perkin Trans. 1, 1263, 1984), to protect thymine (uracil) residues and to protect guanine residues both on the 2-amino and on the 1,6-lactam functions. It may therefore be desirable to replace the monomeric phosphorothioate building blocks 24c and 34c by the corresponding building blocks 38 and 39, respectively, using essentially an aglycone protecting group strategy, (see, for example, Kamimura, T., et al, J. Am. Chem. Soc., 106, 4552, 1984). Studies have shown that both of the latter monomers 38 and 39 are readily accessible in good yields. As indicated above, there has now been completed an informed first stage of a general strategy for the synthesis of oligonucleotide phosphorothioates in solution in that a suitable protecting group for the internucleotide linkages has been identified and methods for the preparation of the required monomeric building blocks (i.e. 34) have been developed. Furthermore, alternative monomeric building blocks of general structure 40 in which the 5'-hydroxy functions are protected with di-(p-anisyl)phenylmethyl, (see, for example, Schaller, H., et al, J. Am. Chem. Soc., 85, 3821, 1963), (DMTr) groups would be expected to be equally suitable. The 9-phenylxanthen-9-yl (Px) protecting group has the advantage that its use generally leads, (see, for example, Chattopadhyaya and Reese, loc cit), to crystalline nucleoside derivatives.

TABLE 1

Data relating to protected 2'-deoxynucleoside 3'-(H-phosphonates) and 2'-deoxynucleoside 3'-phosphorothioate S-(2-cyanoethyl) esters

| Entry No. | Compound | % Yield | $^{31}$P NMR$^a$ | $R_t$ (min)$^b$ |
|---|---|---|---|---|
| 1 | 23 | 98 | 1.0 (d, $J_{P,H}$ 592) | 9.42 |
| 2 | 24c | 92 | 12.7 (s) | 10.43 |
| 3 | 33a | 98 | 0.9 (d, $J_{P,H}$ 587) | 10.05 |
| 4 | 34a | 88 | 12.7 (s) | 11.01 |
| 5 | 33b | 86 | 0.6 (d, $J_{P,H}$ 597) | 11.36 |
| 6 | 34b | 92 | 12.8 (s) | 12.29 |
| 7 | 33c | 72 | 0.4 (d, $J_{P,H}$ 593) | 10.31 |
| 8 | 34c | 93 | 12.6 (s) | 11.13 |

$^a$NMR spectra were measured at 145.8 MHz in $(CD_3)_2SO$
$^b$HPLC was carried out on a Jones Apex Octyl 10µ column which was eluted with 0.1 mol dm$^{-3}$ triethylammonium acetate buffer-acetonitrile mixtures according to programme 1 (see Experimental).

BRIEF DESCRIPTION OF FIGURE

HPLC profiles [Jones APEX Octyl 10µ column eluted with 0.1 mol dm$^{-3}$ triethylammonium acetate (pH 7.0)/acetonitrile according to programme 1 (see Experimental below)] of the triethylammonium salt of O-[3'-O-acetylthymidin-5-yl] O[5'-O-(9-phenylxanthen-9-yl)thymidin-3-yl] phosphorothioate 29 generated (a) by the action of toluene-4-thiol and triethylarnine on the fully-protected dinucleoside phosphorothioate S-(4-nitrobenzyl) ester 28a in acetonitrile solution and (b) the action of tert-butylamine on the fully-protected dinucleoside phosphorothioate S-(2-cyanoethyl) ester 28c in dry pyridine solution.

The following further illustrates the present invention:

Figure 1:
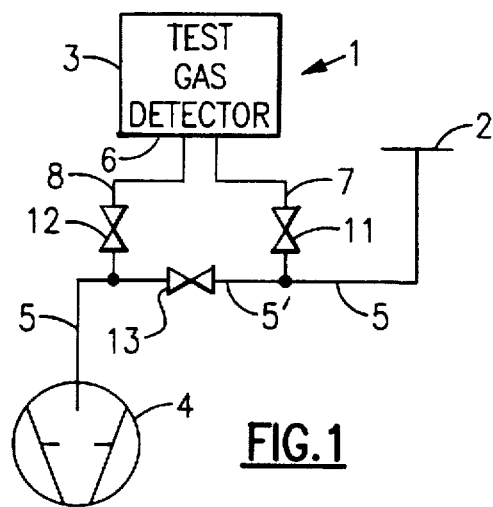
Figure 2:
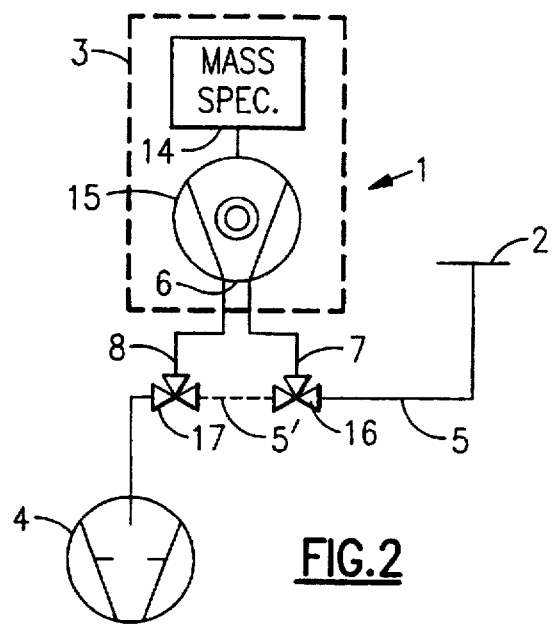
Figure 3:
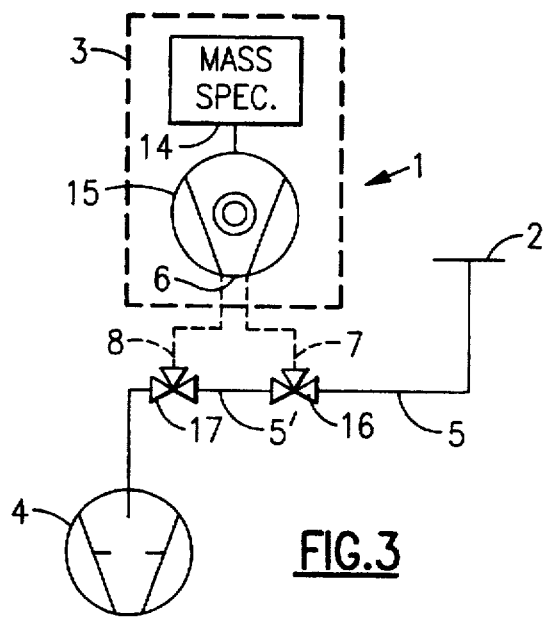
Figure 4:
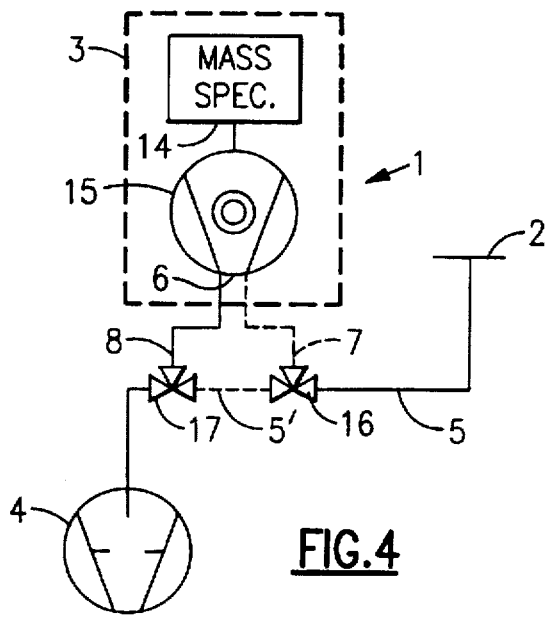

EXPERIMENTAL $^1$H and $^{13}$C NMR spectra were measured, unless otherwise stated, at 360.1 and 90.6 MHz, respectively, using a Bruker AM 360 spectrometer; tetramethylsilane was used as internal standard. $^{31}$P NMR spectra were measured at 145.8 MHz using the same spectrometer. Merck silica gel 60 F$_{254}$ pre-coated plates (Art 5715 and 5642), which, unless otherwise indicated, were developed in solvent system A [chloroform-methanol (9:1 v/v)], were used for thin layer chromatography (TLC). Liquid chromatography (HPLC) was carried out on a Jones Apex Octyl 10µ column which was eluted with 0.1 mol dm$^{-3}$ triethylammonium acetate buffer/acetonitrile mixtures: programme 1 involved a linear gradient over 10 min (flow rate 1.5 cm$^3$ min$^{-1}$) starting with buffer-acetonitrile (7:3 v/v) and ending with buffer-acetonitrile (3:7 v/v); programme 2 involved a linear gradient over 20 min (flow rate 1.5 cm$^3$ min$^{-1}$) starting with buffer-acetonitrile (19:1 v/v) and ending with buffer-acetonitrile (4:1 v/v). Merck Kieselgel H (Art 7736) silica gel was used for short column chromatography. Acetonitrile, pyridine, tetrahydrofuran (THF) and triethylamine were dried by heating, under reflux, with calcium hydride for 3-5 h; dichloromethane was dried by heating, under reflux, over phosphorus pentoxide. These solvents were then distilled at atmospheric pressure and stored over molecular sieves (no. 4A).

N-(4-nitrobenzylmercapto)succinimide 18

Thioacetic acid (20 cm$^3$, 0.28 mol) and anhydrous pyridine (15.2 cm$^3$, 0.188 mol) were added to a solution of 4-nitrobenzyl chloride (12.0 g, 70 mmol) in anhydrous tetrahydrofuran (200 cm$^3$). The stirred reactants were heated at 50° C. for 24 h. The cooled products were filtered and the filtrate was evaporated under reduced pressure. The residue was dissolved in dichloromethane (300 cm$^3$) and the resulting solution was washed with saturated aqueous sodium hydrogen carbonate (2×250 cm$^3$), dried (MgSO$_4$) and concentrated under reduced pressure. The residue was crystallized from ethyl acetate—petroleum ether (bp 60°-80° C.) to give 4-nitrobenzyl thioacetate 16a (11.43 g, 77%) as pale yellow needles, m.p. 55.5°-57.5° C.

Concentrated sulfuric acid—water (1:1 v/v; 17 cm$^3$) was added to a stirred suspension of 4-nitrobenzyl thioacetate (8.0 g, 37.9 mmol) in methanol (150 cm$^3$) and the reactants were heated, under reflux, for 3 h. The cooled products were poured into water (1.0 dm$^3$) and the resulting mixture was extracted with diethyl ether (2×400 cm$^3$). The combined organic extracts were washed with water (2×200 cm$^3$), dried (MgSO$_4$) and evaporated under reduced pressure to give 4-nitrobenzyl mercaptan 17a as a pale yellow solid (6.31 g, 98%).

Lead (II) acetate trihydrate (0.759 g, 2.0 mmol) and 4-nitrobenzyl mercaptan (0.745 g, 4.4 mmol) were stirred together in methanol (24 cm$^3$) solution at room temperature. After 1 h, the products were filtered and the residue was washed with a small volume of cold methanol. The residue was dried in vacuo over calcium chloride and then suspended in dry acetonitrile (20 cm$^3$). Following the evaporation of the solvent under reduced pressure, the residue was suspended in dry benzene (20 cm$^3$) and the solvent was again evaporated under reduced pressure. Finally, the residue was re-suspended in dry benzene (64 cm$^3$) and N-bromosuccinimide (0.783 g, 4.4 mmol) was added in three portions over a period of 45 min to the stirred suspension at room temperature. The reactants were then heated at 50° C., under an atmosphere of argon, for 14 h. The cooled products were filtered and the filtrate was evaporated under reduced pressure to give a solid. The latter material was crystallized from ethyl acetate—hexane to give N-(4-nitrobenzylmercapto)succinimide 18 (0.76 g, 65%) (Found: C, 49.85; H, 3.8; N, 10.4. C$_{11}$H$_{10}$N$_2$O$_4$S requires: C, 49.6; H, 3.8; N, 10.5%), m.p. 146°-148° C.; $\delta_H$[CDCl$_3$] 2.73 (4 H, s), 4.18 (2 H, s), 7.50 (2 H, m), 8.17 (2 H, m); $\delta_C$[CDCl$_3$] 28.4, 40.5, 123.8, 130.3, 141.9, 147.5, 176.2.

Di-(2,4-dinitrobenzyl) disulfide 19, (see, for example, Zhao, loc. cit.)

Redistilled thioacetic acid (25.73 cm$^3$, 0.36 mol) and then dry pyridine (19.9 cm$^3$, 0.246 mol) were added to a stirred solution of 2,4-dinitrobenzyl chloride (13.0 g, 60.0 mmol) in dry THF (180 cm$^3$) at room temperature. After 2 h, the products were filtered and the filtrate was concentrated under reduced pressure. The residual solid obtained was dissolved in dichloromethane (300 cm$^3$) and the resulting solution was washed in turn with saturated aqueous sodium hydrogen carbonate (300 cm$^3$), 1.0 mol dm$^{-3}$ sulfuric acid (200 cm$^3$) and saturated aqueous sodium hydrogen carbonate (200 cm$^3$). The dried (MgSO$_4$) organic layer was evaporated under reduced pressure and the residue was crystallized from ethyl acetate—petroleum ether (b.p. 60°-80° C.) to give S-(2,4-dinitrobenzyl) thioacetate 16b as a pale yellow solid (12.32 g, 80%) (Found: C, 42.3; H, 3.1; N, 10.9. C$_9$H$_8$N$_2$O$_5$S requires: C, 42.2; H, 3.15; N, 10.9%), m.p. 78°-79° C.; $\delta_H$[CDCl$_3$] 2.35 (3 H, s), 4.49 (2 H, s), 7.91. (1 H, d, J 8.5), 8.41 (1 H, dd, J 2.4 and 8.5), 8.88 (1 H, d; J 2.3); $\delta_C$[CDCl$_3$] 30.2, 30.7, 120.7, 127.6, 134.2, 140.6, 147.1, 148.0, 194.7.

A stirred suspension of S-(2,4-dinitrobenzyl) thioacetate 16b (8.2 g, 32 mmol) in concentrated sulfuric acid—water (1:1 v/v; 14.08 cm$^3$) and methanol (128 cm$^3$) was heated, under reflux, for 1.5 h. The cooled products were poured into water (300 cm$^3$) and the resulting mixture was extracted with ether (2×400 cm$^3$). The combined organic extracts were washed with water (300 cm$^3$), dried (MgSO$_4$) and evaporated under reduced pressure to give 2,4-dinitrobenzyl mercaptan 17b as a yellow oil (6.75 g, 98 %) (Found: M$^+$=214.0084 $^{12}$C$_1^1$H$_6^{14}$N$_2^{16}$O$_4^{32}$S requires: 214.0048); $\delta_H$[CDCl$_3$] 2.21 (1 H, t, J 8.7), 4.10 (2 H, d, J 8.7), 7.75 (1 H, d, J 8.7), 8.44 (1 H, dd, J 2.4 and 8.5), 8.77 (1 H, d, J 2.4); $\delta_C$[CDCl$_3$] 26.2, 121.0, 127.8, 133.0, 143.6, 146.9, 148.0.

A solution of iodine (0.321 g, 1.26 mmol) and 2,4-dinitrobenzyl mercaptan (0.493 g, 2.3 mmol) in dichloromethane (25 cm$^3$) was stirred at room temperature overnight. More dichloromethane (25 cm$^3$) was added and the products were washed with 0.2 mol dm$^{-3}$ sodium hydrogen sulfite (20 cm$^3$), water (20 cm$^3$) and saturated aqueous sodium hydrogen carbonate (20 cm$^3$). The dried (MgSO$_4$) organic layer was concentrated under reduced pressure and the residue was crystallized from absolute ethanol to give di-(2,4-dinitrobenzyl) disulfide 19 (0.402 g, 82%) (Found: C, 39.4; H, 2.4; N, 13.0. C$_{14}$H$_{10}$N$_4$O$_8$S$_2$ requires: C, 39.4; H, 2.4; N, 13.1%), m.p. 108°–109° C.; $\delta_H$[CDCl$_3$] 4.22 (4 H, s), 7.66 (2 H, d, J 8.5), 8.46 (2 H, dd, J 2.4 and 8.4), 8.91 (2H, d, J2.4);$\delta_C$[CDCl$_3$] 40.0, 121.1, 127.5, 133.9, 139.4, 147.4, 148.0.

N-(2-cyanoethylmercapto)phthalimide 21

A Solution of chlorine in dichloromethane (1.4 mol dm$^{-3}$, 10.0 cm$^3$, 14.0 mmol) was added dropwise to a stirred solution of 2-cyanoethyl mercaptan, (see, for example, Bauer and Welsh, loc cit), (1.22 g, 14.0 mmol) in dichloromethane (21 cm$^3$) at 0° C. (ice-water bath). After the products had been allowed to warm to room temperature, they were added dropwise to a stirred slurry of phthalimide (1.47 g, 10.0 mmol) and triethylamine (1.94 cm$^3$, 14.0 mmol) in dry DMF (12 cm$^3$) at 0° C. (ice-water bath). The stirred reactants were allowed to warm to room temperature. After 2 h, the products were poured into saturated aqueous sodium hydrogen carbonate (25 cm$^3$) and the resulting mixture was extracted with dichloromethane (2×50 cm$^3$). The combined organic layers were dried (MgSO$_4$) and concentrated under reduced pressure. The residue was crystallized from ethanol to give N-(2-cyanoethylmercapto) phthalimide 21 as colourless needles (1.345 g, 58%) (Found: C, 57.0; H, 3.4; N, 11.8. C$_{11}$H$_8$N$_2$O$_2$S requires: C, 56.9; H, 3.5; N, 12.1%), m.p. 162°–164° C.; $\delta_H$[CDCl$_3$] 2.79 (2 H, t, J7.2), 3.12 (2 H, t, J7.2), 7.83 (2 H, m), 7.95 (2 H, m); $\delta_C$[CDCl$_3$] 18.7, 34.5, 117.5, 124.1, 131.7, 134.9, 168.1.

Triethylammonium salt of 5'-O-(9-phenylxanthen-9-yl)thymidine 3'-(H-phosphonate) 23

Triethylamine (9.04 cm$^3$, 65.0 mmol) and phosphorus trichloride (1.75 cm$^3$, 20.1 mmol) were added to a stirred solution of 1,2,4-1H-triazole (4.14 g, 60.0 mmol; recrystallized from dry acetonitrile) in dry THF (120 cm$^3$) at –35° C. (methanol-dry ice bath). After 15 min, a solution of 5'-O-(9-phenylxanthen-9-yl)thymidine, (see, for example, Chattopadhyaya and Reese, loc cit), (2.49 g, 5.0 mmol) in THF (100 cm$^3$) was added. After a further period of 15 min, triethylamine-water (1:1 v/v; 25 cm$^3$) was added and the reactants were allowed to warm to room temperature. The products were then evaporated under reduced pressure. The residue was dissolved in chloroform (300 cm$^3$) and the solution was washed with 0.5 mol dm$^{-3}$ triethylammonium bicarbonate buffer (pH 7.5, 2×150 cm3). The organic layer was dried (MgSO$_4$) and evaporated under reduced pressure. Toluene (25 cm$^3$) was added and then removed by evaporation to give a glass that was then fractionated by short column chromatography on silica gel: appropriate fractions, which were eluted with chloroform-methanol (90:10–85:15 v/v), were combined and evaporated under reduced pressure. A solution of the residue in chloroform (30 cm$^3$) was added dropwise with stirring to light petroleum (b.p. 30°–40° C.) (75.0 cm$^3$) to give the triethylammonium salt of 5'-O-(9-phenylxanthen-9-yl)thymidine 3'-(H-phosphonate) 23 (3.273g, 98%) as a colourless precipitated solid; R$_t$ 9.42 min (programme 1); $\delta_H$[(CD$_3$)$_2$SO] includes the following signals: 1.42 (3 H, s), 2.38 (2 H, m), 3.13 (1 H, dd, J=3.5 and 10.3), 3.19 (1 H, dd, J=3.1 and 10.3), 4.04 (1 H, m), 4.76 (1 H, m), 6.19 (1 H, t, J=6.8), 6.62 (1 H, d, J$_{P,H}$592), 7.05–7.45 (13 H, m), 7.57 (1 H, s), 11.41 (1 H, s); $\delta_P$[(CD$_3$)$_2$SO] 1.0 (d, J$_{P,H}$592).

Triethylammonium salt of 5'-O-(9-phenylxanthen-9-yl)thymidine 3'-phosphorothioate S-(4-nitrobenzyl) ester 24a.

A solution of the triethylammonium salt of 5'-O-(9-phenylxanthen-9-yl)thymidine 3'-(H-phosphonate) 23 (0.664 g, 1.0 mmol) and N-(4-nitrobenzylmercapto) succinimide (0.346 g, 1.3 mmol) in dichloromethane-acetonitrile (2:1 v/v; 15 cm$^3$) was evaporated to dryness under reduced pressure. The residue was redissolved in dichloromethane-acetonitrile (2:1 v/v; 15 cm$^3$) and the solution was again evaporated under reduced pressure. The residue was then dissolved in dry dichloromethane (20 cm$^3$), and triethylamine (0.835 cm$^3$, 6.0 mmol) and chlorotrimethylsilane (0.508 cm$^3$, 4.0 mmol) were added to the stirred solution at room temperature. After 2.5 h, the products were poured into 0.2 mol dm$^{-3}$ aqueous triethylammonium hydrogen carbonate (200 cm$^3$), and the resulting mixture was extracted with dichloromethane (200 cm$^3$, followed by 2×100 cm$^3$). The dried (MgSO$_4$) combined organic extracts were concentrated under reduced pressure and the residue was fractionated by short column chromatography on silica gel: the appropriate fractions, eluted with chloroform-methanol (88:12 v/v), were combined and evaporated under reduced pressure. A solution of the residue in chloroform (6 cm$^3$) was added dropwise to stirred petroleum ether (b.p. 30°–40° C., 150 cm$^3$) at room temperature to give the triethylammonium salt of 5'-O-(9-phenylxanthen-9-yl) thymidine 3'-phosphorothioate S-(4-nitrobenzyl) ester 24a as a pale yellow solid (0.72 g, 86%); R$_t$ 11.87 min (programme 1); $\delta_H$[(CD$_3$)$_2$SO] includes the following signals: 1.39 (3 H, d, J 0.8), 2.15–2.4 (2 H, m), 2.91 (1H, dd, J=3.5 and 10.2), 3.82 (2 H, m), 3.92 (1 H, m), 4.68 (1 H, m), 6.14 (1 H, dd, J=5.8 and 8.6), 7.0–7.45 (13 H, m), 7.50 (2 I-I, m), 7.54 (1 H, m), 8.03 (2 H, m), 11.37 (1 H, s), $\delta_P$[(CD$_3$)2SO] 13.4.

Triethylammonium salt of 5'-O-(9-phenylxanthen-9-yl) thymidine 3'-phosphorothioate S-(2,4-dinitrobenzyl) ester 24b A solution of the triethylammonium salt of 5'-O-(9-phenylxanthen-9-yl)thymidine 3'-(H-phosphonate) (0.199 g, 0.3 mmol) and di-(2,4-dinitrobenzyl) disulfide (0.153 g, 0.36 mmol) in dichloromethane-acetonitrile (1:1 v/v, 6 cm$^3$) was evaporated to dryness under reduced pressure. The residue was dissolved in the same solvent mixture (6 cm$^3$), and the solution was again evaporated under reduced pressure. The residue was then dissolved in dry dichloromethane (6 cm$^3$), and 4-methylmorpholine (0.34 cm$^3$, 3.1 mmol) and chlorotrimethylsilane (0.15 cm$^3$, 1.2 mmol) were added to the stirred solution at room temperature. After 3 h, the products were poured into 0.5 mol dm$^{-3}$ aqueous triethylammonium hydrogen carbonate (50 cm$^3$), and the resulting mixture was extracted with dichloromethane (2×50 cm$^3$). The dried (MgSO$_4$) combined organic extracts were concentrated under reduced pressure and the residue was fractionated by short column chromatography on silica gel: the appropriate fractions, elated with chloroform-methanol (9:1 v/v) were combined and evaporated under reduced pressure. A solution of the residue in chloroform (2 cm$^3$) was added dropwise to stirred petroleum ether (b.p. 30°–40° C., 50 cm$^3$) at room temperature to give the triethylammonium salt of 5'-O-(9-phenylxanthen-9-yl)thymidine 3'-phosphorothioate S-(2,4-dinitrobenzyl) ester 24b (0.177 g, 67%); R$_t$ 10.17 min (programme 1); δ$_H$[(CD$_3$)$_2$SO] includes the following signals: 1.40 (3 H, s), 2.25 (2 H, m), 3.08 (1 H, dd, J 3.2 and 10.6), 3.97 (1 H, m), 4.11 (2 H, m), 4.65 (1 H, m), 6.08 (1 H, t, J 7.2), 6.95–7.5 (13 H, m), 7.53 (1 H, s), 7.92 (1 H, d, J 8.6), 8.41 (1 H, dd, J 2.4 and 8.5), 8.63 (1 H, d, J 2.4),11.36 (1 H, br s); δ$_P$[(CD$_3$)$_2$SO] 12.4.

Triethylammonium salt of 5'-O-(9-phenylxanthen-9-yl)thymidine 3'-phosphorothioate S-(2-cyanoethyl) ester 24c A solution of the triethylammonium salt of 5'-O-(9-phenylxanthen-9-yl)thymidine 3'-(H-phosphonate) 23 (0.199 g, 0.3 mmol) and N-(2-cyanoethylmercapto)phthalimide (0.091 g, 0.4 mmol) in dichloromethane-acetonitrile (2:1 v/v, 6 cm$^3$) was evaporated to dryness under reduced pressure. The residue was dissolved in the same solvent mixture (6 cm$^3$), and the solution was again evaporated under reduced pressure. The residue was then dissolved in dry dichloromethane (6 cm$^3$), and 4-methylmorpholine (0.206 cm$^3$, 1.9 mmol) and chlorotrimethylsilane (0.15 cm$^3$, 1.2 mmol) were added to the stirred solution at room temperature. After 3 h, the products were worked up, and purified as in the above preparation of the corresponding S-(2,4-dinitrobenzyl) ester. The triethylammonium salt of 5'-O-(9-phenylxanthen-9-yl)thymidine 3'-phosphorothioate S-(2-cyanoethyl) ester 24c was isolated as a colourless precipitated solid (0.208 g, 92%); R$_t$ 10.43 min (programme 1); δ$_H$[(CD$_3$)$_2$SO] includes the following signals: 1.41 (3 H, d, J 0.7), 2.40 (2 H, m), 2.67 (2 H, m), 2.84 (2 H, m), 3.14 (1 H, dd, J3.6and 10.2), 3.19 (1 H, dd, J3.0 and 10.2), 4.15 (1 H, m), 4.81 (1 H, m), 6.21 (1 H, dd, J6.1 and 8.2), 7.05–7.5 (13 H, m), 7.59 (1 H, m), 11.41 (1 H, s); δ$_P$[(CD$_3$)$_2$SO] 12.7.

Triethylammonium salt of O-[3'-O-acetylthymidin-5-yl] O-[5'-O-(9-phenylxanthen-9-yl)thymidin-3-yl] phosphorothioate 29. (a)

A solution of the triethylammonium salt of 5'-O-(9-phenylxanthen-9-yl)thymidine 3'-phosphorothioate S-(4-nitrobenzyl) ester 24a (0.299 g, 0.36 mmol), 3'-O-acetylthymidine, (see, for example, Horwitz, et al, loc cit, 26 (0.085 g, 0.3 mmol) and 3-nitro-1,2,4-1H-triazole, (see, for example, Jones, et al, loc cit), (0.171 g, 1.5 mmol) in dry pyridine (5 cm$^3$) was evaporated under reduced pressure. The residue was redissolved in dry pyridine (5 cm$^3$) and the solution was re-evaporated. After this process had been repeated once more, the residue was dissolved in dry pyridine (3 cm$^3$) and solid mesitylene-2-sulfonyl chloride (0.229 g, 1.05 mmol) was added. After the reaction solution had been stirred at room temperature for 50 min, saturated aqueous sodium hydrogen carbonate (0.5 cm$^3$) was added and the products were partitioned between dichloromethane (20 cm$^3$) and 0.2 mol dm$^{-3}$ aqueous triethylammonium hydrogen carbonate. The layers were separated and the aqueous layer was extracted with dichloromethane (2×10 cm$^3$). The combined organic layers were dried (MgSO$_4$) and concentrated under reduced pressure. The residue was coevaporated with toluene (5 cm$^3$) and the residue was fractionated by short column chromatography on silica gel: appropriate fractions, which were eluted with chloroform-methanol (99:1 to 98:2 v/v), were combined and evaporated under reduced pressure. A solution of the residue in chloroform (2 cm$^3$) was added dropwise with stirring to petroleum ether (b.p. 30°–40° C., 50 cm$^3$) to give the fully-protected dinucleoside phosphorothioate S-(4-nitrobenzyl) ester 28a as a precipitated solid (0.254 g, 85%); δ$_P$[(CD$_3$)$_2$SO] 27.47, 27.61. Toluene-4-thiol (0.062 g, 0.5 mmol) and then triethylamine (0.035 cm$^3$, 0.25 mmol) were added to a stirred solution of the latter material (0.50 g, 0.05 mmol) in dry acetonitrile (2.8 cm$^3$) at room temperature. After 4.5 h, allyl chloride (0.5 cm$^3$, 6.1 mmol) was added and, after a further period of 5 min, the products were evaporated under reduced pressure. HPLC analysis revealed no starting material 28a and four nucleotide or nucleoside products with the following R$_t$s (programme 1): 10.73 (37.5 %), 10.98 (60.55%), 11.87 (0.8%), 12.05 min (1.14%). The two lower R$_t$ components were believed to be the desired diasiereoisomeric partially-protected dinucleoside phosphorothioates 29 and the other two components (R$_t$s 11.87 and 12.05 min) corresponded to 5'-O-(9-phenylxanthen-9-yl)thymidine 3'-phosphorothioate S-(4-nitrobenzyl) ester 24a and 3'-O-acetyl-5'-S-(4-methylphenyl)-5'-thiothymidine 31, respectively. The products were fractionated by short column chromatography on silica gel: appropriate fractions, which were elutect with chloroform-methanol (85:15 v/v), were combined and evaporated under reduced pressure. A solution of the residue in chloroform (1 cm$^3$) was added to stirred petroleum ether (b.p. 30°–40 ° C., 50 cm$^3$) to give the triethylammonium salt of O-[3'-O-acetylthymidin-5-yl]O-[5'-O-(9-phenylxanthen-9-yl)thymidin-3-yl] phosphorothioate 29 (0.047 g, 97%) as a colourless precipitate; δ$_P$[(CD$_3$)$_2$SO] 53.99, 54.07.

(b) A dry solution of the triethylammonium salt of 5'-O-(9-phenylxanthen-9-yl)thymidine 3'-phosphorothioate S-(2-cyanoethyl) ester 24c (0.269 g, 0.36 mmol), 3'-O-acetylthymidine 26 (0.085 g, 0.3 mmol) and 3-nitro-1,2,4-1H-triazole (0.239 g, 2.1 mmol) in pyridine (3 cm$^3$) was prepared by the procedure described in section (a) above. Mesitylene-2-sulfonyl chloride (0.229 g, 1.05 mmol) was added to the stirred solution at room temperature and the reaction was allowed to proceed for 40 min. The products were then worked-up and fractionated according to the above procedure [section (a)] to give the fully-protected dinucleoside phosphorothioate S-(2-cyanoethyl) ester 28e which was isolated as a colourless precipitated solid (0.246 g, 90%); δ$_P$[(CD$_3$)$_2$SO] 27.62, 27.94. t-butylamine (0.20 cm$^3$, 1.9 mmol) was added to a stirred solution of the latter material (0.046 g, 0.05 mmol) in dry pyridine (0.8 cm$^3$) at room temperature. After 100 min, the products were evaporated under reduced pressure, redissolved in chloroform (25 cm$^3$) and the resulting solution was washed with 0.5 mol dm$^{-3}$ triethylammonium hydrogen Carbonate (2×15 cm$^3$). The dried (MgSO$_4$) organic layer was filtered and concentrated under reduced pressure. A solution of the residue in chloroform (1 cm$^3$) was added to stirred petroleum ether (b.p. 30°–40° C., 50 cm$^3$) to give the triethylammonium salt of O-[3'-O-acetylthymidin-5-yl] O-[5'-O-(9-phenylxanthen-9-yl)thymidin-3-yl] phosphorothioate 29 (0.048 g, 99%) as a colourless precipitated solid; $R_t$ (programme 1) 10.69, 10.93 min; $\delta_P[(CD_3)_2SO]$ 54.60, 54.94.

3'-O-acetyl-5'-S-(4-methylphenyl)-5'-thiothymidine 31

A solution of 3'-O-acetylthymidine 26 (0.511 g, 1.8 mmol) and toluene-4-sulfonyl chloride (0.514 g, 2.7 mmol) in dry pyridine (3 cm$^3$) was stirred at room temperature. After 16 h, saturated aqueous sodium hydrogen carbonate (2 cm$^3$) was added and, after a further 10 min, the products were partitioned between chloroform (50 cm$^3$) and saturated aqueous sodium hydrogen carbonate (50 cm$^3$). The dried (MgSO$_4$) organic layer was concentrated under reduced pressure. The residue was fractionated by short column chromatography on silica gel: the appropriate fractions, eluted with chloroform-methanol (99:1 v/v), were combined and evaporated under reduced pressure. The residue was dissolved in acetonitrile (2.5 cm$^3$) at room temperature and triethylamine (0.90 cm$^3$, 6.5 mmol) and toluene-4-thiol (0.805 g, 6.5 mmol) were added to the stirred solution which was kept under an atmosphere of argon. After 60 h, the products were concentrated under reduced pressure and the residue was fractionated by short column chromatography on silica gel: the appropriate fractions, eluted with chloroform-methanol (99:1 v/v) were combined and evaporated under reduced pressure to give 3'-O-acetyl-5'-S-(4-methylphenyl)-5'-thiothymidine 31 as a colourless glass (0.60 g, 85% based on 3'-O-acetylthymidine) (Found: M$^+$=390.1249. $^{12}C_{19}^{1}H_{22}^{14}N_2^{16}O_5^{32}S$ requires: 390.1249); $R_t$ 12.05 min (programme 1); $\delta_H[(CD_3)2SO]$ 1.76 (3 H, d, J0.9), 2.05 (3 H, s), 2.25 (1 H, m), 2.26 (3 H, s), 2.49 (1 H, m), 3.32 (2 H, m), 4.02 (1 H, m), 5.18 (1 H, m), 6.13 (1 H, dd, J 6.0, 8.6), 7.14 (2 H, d, J7.9), 7.29 (2 H, d, J 8.2), 7.51 (1 H, m), 11.38 (1 H, br s); $\delta_C[(CD_3)_2SO]$ 12.1, 20.5, 20.8, 35.2, 35.4, 75.7, 81.9, 83.9, 110.0, 129.1, 129.7, 131.6, 135.7, 136.0, 150.5, 163.6, 169.9.

Triethylammonium salt of O-[thymidin-5-yl] O-[thymidin-3-yl] phosphorothioate 30

The triethylammonium salt of O-[3'-O-acetylthymidin-5-yl] O-[5'O-(9-phenylxanthen-9-yl)thymidin-3-yl] phosphorothioate 29 (0.036 g, ca. 0.037 mmol), prepared from its S-(2-cyanoethyl) ester 28c, was dissolved in concentrated aqueous ammonia (d 0.88, 4 cm$^3$) at room temperature. The solution was stirred for 40 min and was then evaporated under reduced pressure. The residue was dissolved in methanol (5 cm$^3$) and the solution was evaporated under reduced pressure. After this process had been repeated with ethanol (3×5 cm$^3$), the residue was dissolved in acetic acid-water (4:96 v/v, 4 cm$^3$) at room temperature. After 4 h, the products were evaporated under reduced pressure and the residue was partitioned between chloroform (10 cm$^3$) and water (5 cm$^3$). The aqueous layer was separated, extracted with chloroform (10 cm$^3$) and then evaporated under reduced pressure. The residue was fractionated on a column (17 cm×2 cm diameter) of DEAE Sephadex A-25 which was eluted with a linear gradient of aqueous triethylammonium hydrogen carbonate buffer (pH 7.5, 0.001–1.0 mol dm$^{-3}$ over 1000 cm$^3$): the appropriate fractions (eluted with an average buffer concentration of 0.28 mol dm$^{-3}$) were combined and evaporated under reduced pressure. The residue was re-evaporated from ethanol (2×10 cm$^3$) solution to give the triethylammonium salt of O-(thymidin-5-yl) O-(thymidin-3-yl) phosphorothioate 30 (554 A$_{265}$ units) as a colourless solid; $R_t$ (programme 2) 14.98, 15.85 min; $\delta_H[D_2O]$ includes the following signals: 1.82 (3 H, s), 1.87 and 1.88 (3 H, 2 s), 2.32 (3 H, m), 2.50 (1 H, m), 3.78 (2 H, m), 4.13 (4 H, m), 4.54 (1 H, m), 4.91 (1 H, m), 6.16 (1 H, m), 6.27 (1 H, t, J 6.9), 7.62 (1 H, s), 7.68.(1 H, s); $\delta_P[D_2O]$ 56.36, 56.00.

Triethylammonium salt of 5'-O-(9-phenylxanthen-9-yl)-6-N-pivaloyl-2'-deoxyadenosine 3'-(H-phosphonate) 33a This compound was prepared on the same scale and in precisely the same way as the simple thymidine derivative 23 described above. 5'-O-(9-phenylxanthen-9-yl)-6-N-pivaloyl-2'-deoxyadenosine; (see for example, Rao and Reese, loc cit), (2.96 g, 5.0 mmol) was converted into the triethylammonium salt of 5'-O-(9-phenylxanthen-9-yl)-6-N-pivaloyl-2'-deoxyadenosine 3'-(H-phosphonate) 33a (3.67 g, 98%). This product was isolated as a colourless precipitated solid; $R_t$10.05 min (programme 1); $\delta_H[(CD_3)_2SO]$ includes the following signals: 1.28 (9 H, s), 2.56 (1 H, m), 3.09 (1 H, dd, J 5.6 and 10.0), 3.28 (1 H, dd, J 4.4 and 10), 4.17 (1 H, m), 4.93 (1 H, m), 6.41 (1 H, t, J 6.7), 6.67 (1 H, d, $J_{P,H}$ 590), 6.82–7.45 (13 H, m), 8.50 (1 H, s), 8.52 (1 H, s), 10.21 (11% s); $\delta_P[(CD_3)_2SO]$ 0.9 (d, $J_{P,H}$587).

Triethylammonium salt of 5'-O-(9-phenylxanthan-9-yl)-6-N-pivaloyl-2'-deoxyadenosine 3'-phosphorothioate S-(2-cyanoethyl) ester 34a This compound was prepared in the same way as the corresponding thyroidinc derivative 24c described above. The triethylammonium salt of 5'-O-(9-phenylxanthen-9-yl)-6-N-pivaloyl-2'-deoxyadenosine 3'-(H-phosphonate) 33a (1.14 g, 1.5 mmol) was converted into the triethylammonium salt of 5'-O-(9-phenylxanthen-9-yl)-6-N-pivaloyl-2'-deoxyadenosine 3'-phosphorothioate S-(2-cyanoethyl) ester 34a (1.12 g, 88%). The product was isolated as a colourless precipitated solid; $R_t$ 11.01 min; $\delta_H H[(CD_3)_2SO]$ includes the following signals: 1.29 (9 H, s), 2.63 (1 H, m), 2.76 (2 H, m), 2.90 (2 H, m), 3.33 (1 H, m), 4.27 (1 H, m), 4.98 (1 tt, m), 6.42 (1 H, t, J=6.9), 6.85–7.45 (13 H, m), 8.5t (1 H, s), 8.53 (1 H, s), 10.20 (1 H, s); $\delta_P[(CD_3)_2SO]$ 12.7.

Triethylammonium salt of 4N-benzoyl-5'-O-(9-phenylxanthen-9-yl)-2'-deoxycytidine 3'-(H-phosphonate) 33b.

This compound was prepared on the same scale and in precisely the same way as the simple thyroidinc derivative 23 described above. 4-N-benzoyl-5'-O-(9-phenylxanthen-9-yl)-2'-deoxycytidine, (see, for example, Chattopadhyaya and Reese, loc cit), (2.94 g, 5.0 mmol) was converted into the triethylammonium salt of 4-N-benzoyl-5'-O-(9-phenylxanthen-9-yl)-2'-deoxycytidine 3'-(H-phosphonate) 33b (3.25 g, 86%). The product was isolated as a colourless precipitated solid; $R_t$ 11.36 min (programme 1); $\delta_H[(CD_3)_2SO+D_2O]$ includes the following signals: 2.33 (1 H, m), 2.59 (1 H, m), 3.12 (1 H, dd, J 3.8 and 10.6), 3.25 (1 H, dd, J 3.2 and 10.6), 4.14 (1 H, m), 4.75 (1 H, m), 6.13 (1 H, t, J 5.9), 6.60 (1 H, d, $J_{P,H}$ 597), 7.1–7.5 (14 H, m), 7.54 (2 H, m), 7.63 (1 H, m), 8.00 (2 H, m), 8.27 (1 H, m); $\delta_P[(CD_3)_2SO]$ 0.6 (d, $J_{P,H}$ 597).

Triethylammonium salt of 4-N-benzoyl-5'-O-(9-phenylxanthen-9-:yl)-2'-deoxycytidine 3'-phosphorothioate S-(2-cyanoethyl) ester 34b This compound was prepared in the same way as the corresponding thymidine derivative 24c described above.

The triethylammonium salt of 4-N-benzoyl-5'-O-(9-phenylxanthen-9-yl)-2'-deoxycytidine 3'-(H-phosphonate) 33b (1.13 g, 1.5 mmol) was converted into the triethylammonium salt of 4-N-benzoyl-5'-O-(9-phenylxanthen-9-yl)-2'-deoxycytidine 3'-phosphorothioate S-(2-cyanoethyl) ester 34b (1.16 g, 92%). The product was isolated as a colourless precipitated solid; $R_t$ 12.29 min (programme 1); $\delta_H[(CD_3)_2SO]$ includes the following signals: 2.28 (1 H, m), 2.67 (3 H, m), 2.85 (2 H, m), 3.14 (1 H, dd, J4.4 and 10.4), 3.23 (1 H, dd, J 3.2 and 10.4), 4.27 (1 H, m), 4.73 (1 H, m), 6.14 (1 H, t, J 6.4), 7.1–7.65 (17 H, m), 8.02 (2 H, d, J 7.4), 8.17 (1 H, d, J 7.5), 11.33 (1 H, br.s); $\delta_P[(CD_3)_2SO]$ 12.8.

Triethylammonium salt of 2-N-phenylacetyl-5'-O-(9-phenylxanthen-9-yl)-2'-deoxyguanosine 3'-(H-phosphonate) 33c.

This compound was prepared on the same scale and in precisely the same way as the simple thyroidine derivative 23 described above. 2-N-phenylacetyl-5'-O-(9-phenylxanthen-9-yl)-2'-deoxyguanosine, (see, for example, Benseler and McLaughlin, loc cit), (3.21 g, 5.0 mmol) was converted into the triethylammonium salt of 2-N-phenylacetyl-5'-O-(9-phenylxanthene-9-yl)-2'-deoxyguanosine 3'-(H-phosphonate) 33c (2.92 g, 72 %). The product was isolated as a colourless precipitated solid; $R_t$ 10.31 min (programme 1); $\delta_H[(CD_3)_2SO]$ includes the following signals: 2.55 (1 H, m), 2.75 (1 H, m), 3.15 (2 H, m), 3.80 (2 H, s), 4.15 (1 H, m), 4.85 (1 H, m), 6.23 (1 H, t, J 6.4), 6.70 (1 H, d, $J_{P,H}$ 596), 6.85–7.45 (18 H, m), 8.01 (1 H, s); $\delta_P[(CD_3)_2SO]$ 0.4 (d, $J_{P,H}$ 593).

Triethylammonium salt of 2-N-phenylacetyl-5'-O-(9-phenylxanthen-9-yl)-2'-deoxyguanosine 3'-phosphorothioate S-(2-cyanoethyl) ester 34c This compound was prepared in the same way as the corresponding thymidine derivative 24c described above. The triethylammoninm salt of 2-N-phenylacetyl-5'-O-(9-phenylxanthen-9-yl)-2'-deoxyguanosine 3'-(H-phosphonate) 33c (1.21 g, 1.5 mmol) was converted into the triethylammonium salt of 2-N-phenylacetyl-5'-O-(9-phenylxanthen-9-yl)-2'-deoxyguanosine 3'-phosphorothioate S-(2-cyanoethyl) ester 34c (1.25 g, 93%). The product was isolated as a colourless precipitated solid; $R_t$ 11.13 min (programme 1); $\delta_H[(CD_3)_2SO]$ includes the following signals: 2.55–2.95 (10 H, m), 3.17 (2 H, m), 3.80 (2 H, s), 4.24 (1 H, m), 4.85 (1 H, m), 6.25 (1 H, t, J 6.9), 6.9–7.45 (18 H, m), 8.01 (1 H, s); $\delta_P[(CD_3)_2SO]$ 12.6.

All the references cited herein are incorporated by reference.

I claim:

1. A process for the production of a nucleoside phosphorothioate derivative corresponding to the following general formula (I):

$$\underset{R^2-S}{\overset{O}{\underset{\|}{\diagdown}}}\overset{O-R^1}{\underset{\diagup}{P}}\overset{}{\underset{O-M^+}{}}\quad (I)$$

wherein it comprises reacting a salt of a nucleoside H-phosphonate corresponding to the following general formula (II):

$$\underset{H}{\overset{O}{\underset{\|}{\diagdown}}}\overset{O-R^1}{\underset{\diagup}{P}}\overset{}{\underset{O-M^+}{}}\quad (II)$$

with a thiol transfer agent corresponding to the following general formula (III):

$$R^2—S—X \quad (III)$$

in the presence of a silylating agent and a base in a suitable solvent; and working-up the reaction mixture to isolate the desired product and change the counter-cation as desired; wherein $M^+$ represents a suitable counter-cation;

$R^1$ represents an appropriate nucleoside or nucleoside analogue;

$R^2$ represents a desired protecting group, which is optionally ultimately removed by cleavage of its bond to the sulfur atom; and X represents a leaving group.

2. A process as claimed in claim 1 wherein $R^2$ represents alkyl, substituted alkyl, aralkyl, substituted aralkyl, alkenyl or substituted alkenyl.

3. A process as claimed in claim 2 wherein $R^2$ represents methyl, 2-cyanoethyl, benzyl, mononitrobenzyl, dinitrobenzyl or allyl.

4. A process as claimed in claim 1 wherein X represents the conjugate base of succinimide or phthalimide, either of which is optionally substituted.

5. A process as claimed in claim 2 wherein X represents the conjugate base of succinimide or phthalimide, either of which is optionally substituted.

6. A process as claimed in claim 3 wherein X represents the conjugate base of succinimide or phthalimide, either of which is optionally substituted.

7. A process as claimed in claim 1 wherein $R^2$ is not removed.

8. A process as claimed in claim 2 wherein $R^2$ is not removed.

9. A process as claimed in claim 3 wherein $R^2$ is not removed.

10. A process as claimed in claim 4 wherein $R^2$ is not removed.

11. A process as claimed in claim 5 wherein $R^2$ is not removed.

12. A process as claimed in claim 6 wherein $R^2$ is not removed.

13. The method of claim 1 wherein the thiol transfer agent is N-(2-cyanoethylmercapto)-phthalimide or N-(2-cyanoethylmercapto)-succinimide.

14. A process for the production of an oligonucleotide phosphorothioate analogue wherein the nucleoside phosphorothioate derivative (I) produced by the process of claim 2 is used in a phosphotriester method.

15. A process for the production of an oligonucleotide phosphorothioate analogue wherein the nucleoside phosphorothioate derivative (I) produced by the process of claim 3 is used in a phosphotriester method.

16. A process for the production of an oligonucleotide phosphorothioate analogue wherein the nucleoside phosphorothioate derivative (I) produced by the process of claim 4 is used in a phosphotriester method.

17. A process for the production of an oligonucleotide phosphorothioate analogue wherein the nucleoside phosphorothioate derivative (I) produced by the process of claim 5 is used in a phosphotriester method.

18. A process for the production of an oligonucleotide phosphorothioate analogue wherein the nucleoside phosphorothioate derivative (I) produced by the process of claim 6 is used in a phosphotriester method.

19. A process for the production of an oligonucleotide phosphorothioate analogue wherein the nucleoside phosphorothioate derivative (I) produced by the process of claim 7 is used in a phosphotriester method.

20. A process for the production of an oligonucleotide phosphorothioate analogue wherein the nucleoside phosphorothioate derivative (I) produced by the process of claim 8 is used in a phosphotriester method.

21. A process for the production of an oligonucleotide phosphorothioate analogue wherein the nucleoside phosphorothioate derivative (I) produced by the process of claim 9 is used in a phosphotriester method.

22. A process for the production of an oligonucleotide phosphorothioate analogue wherein the nucleoside phosphorothioate derivative (I) produced by the process of claim 10 is used in a phosphotriester method.

23. A process for the production of an oligonucleotide phosphorothioate analogue wherein the nucleoside phosphorothioate derivative (I) produced by the process of claim 11 is used in a phosphotriester method.

24. A process for the production of an oligonucleotide phosphorothioate analogue wherein the nucleoside phosphorothioate derivative (I) produced by the process of claim 11 is used in a phosphotriester method.

25. A process for the production of an oligonucleotide phosphorothioate analogue wherein the nucleoside phosphorothioate derivative (I) produced by the process of claim 12 is used in a phosphotriester method.

* * * * *

UNITED STATES PATENT AND TRADEMARK OFFICE
CERTIFICATE OF CORRECTION

PATENT NO.    : 5,708,161
DATED         : January 13, 1998
INVENTOR(S)   : Colin Bernard Reese.

It is certified that error appears in the above-identified patent and that said Letters Patent is hereby corrected as shown below:

The sheet of drawing, consisting of figures 1-4 should be deleted, to appear as per attached figures 1A-B.

The title page, should be deleted

Signed and Sealed this

Twenty-ninth Day of December, 1998

Attest:

BRUCE LEHMAN

Attesting Officer

Commissioner of Patents and Trademarks

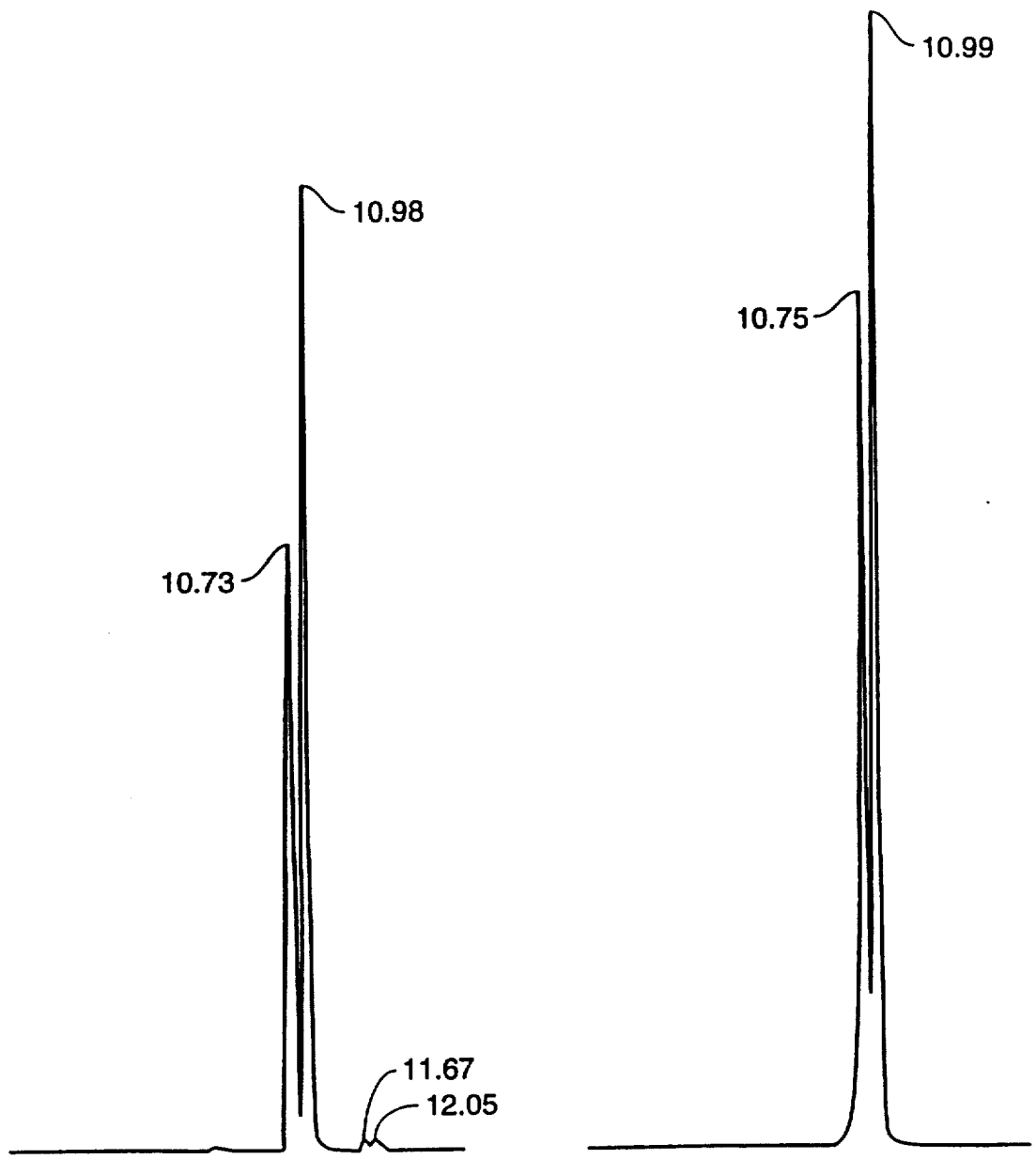
*FIG._1A*  *FIG._1B*

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 2, line 56, "et at," should read — et al. —;
line 60, "quantifies" should read — quantities —;
line 65, "couplirig" should read — coupling —;

Column 4, line 30, "2" should read — 2 —;
line 32, "3" should read — 3 —;
line 33, "4" should read — 4 —;
line 34, "2" should read — 2 —;
line 35, "2" should read — 2 —;
line 36, "6" should read — 6 —;
line 38, "6" should read — 6 —;
line 39, "7" should read — 7 —;
line 44, "3" should read — 3 —;
line 45, "4" should read — 4 —;
line 50, "Firsfly" should read — Firstly —;
line 51, "2" should read — 2 —;
line 54, "4" should read — 4 —;

Column 5, line 35, "a; X=S,$R^1R^2$=Cl" should read — a; X=S, $R^1$=$R^2$=Cl —;
line 44, "8a" should read — 8a —;
line 46, "8b" should read — 8b —;
line 51, "p-thiocresoI," should read — *p*-thiocresol —;
line 59, "8" should read — 8 —;
line 62, "8b" should read — 8b —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 6, line 1, "laworska" should read — Jaworska —;
line 2, "8c" should read — 8c —;
line 5, "9" should read — 9 —;
line 13, "8d" should read — 8d —;
line 14, "Reese,." should read — Reese, —, and "Tel. Lett.," should read — Tet. Lett., —;
line 16, "8c" should read — 8c —, and "8" should read — 8 —;
line 17, "9" should read — 9 —;
line 33, "13" should read — 13 —;
line 34, "14" should read — 14 —;
line 37, "199.0)" should read — 1990) —;
line 38, "10" should read — 10 —;
line 39, "13" should read — 13 —;
line 41, "11" should read — 11 —;
line 43, "12" should read — 12 —;
line 45, "14" should read — 14 —;
line 47, "13" should read — 13 —;
line 52, both instances of "13" should read — 13 —;
line 61, "13 or 14" should read — 13 or 14 —;
line 62, "17a, 17b" should read — 17a, 17b —;
line 63, "20" should read — 20 —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 7, line 44, "50° C.," should read — 50°C, —;
line 45, 0° C.," should read — 0°C, —;
line 51, "17a and 17b," should read — 17a and 17b, —;
line 53, "15a" should read — 15a —;
line 54, "50° C.," should read — 50°C, —;
line 55, "16a" should read — 16a —;
line 56, "16a" should read — 16a —;
line 57, "17a" should read — 17a —;
line 59, "17b" should read — 17b —;
line 62, "15b" should read — 15b —;
line 63, "18" should read — 18 —;
Column 8, line 3, "17a" should read — 17a —;
line 5, "17b" should read — 17b —;
line 6, "13" should read — 13 —;
line 7, "14" should read — 14 —;
line 8, "19" should read — 19 —;
line 12, "17b" should read — 17b —;
line 14, "20" should read — 20 —;
line 19, "21" should read — 21 —;
Column 9, line 16, "-35° C.," should read — -35°C, —, and "24a:" should read — 24a: —;
line 17, "18" should read — 18 —, and "24b: 19" should read — 24b: 19 —;
line 18, "24c: 21" should read — 24c: 21 —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 9, line 19, "4-methylmoxpholine" should read
— 4-methylmorpholine —; and "Et NH$^+$ HCO$_3$—." should read — Et$_3$NH$^+$ HCO$_3^-$. —;
line 21, "22" should read — 22 —;
line 24, "24a, 24b and 24c" should read — 24a, 24b and 24c —;
line 25, "22" should read — 22 —;
line 26, "from-phosphorous" should read — from phosphorous —;
line 28, "-35° C.," should read — -35°C, —;
line 32, "23" should read — 23 —;
line 34, "23" should read — 23 —;

Column 10, line 1, "23" should read — 23 —;
line 2, "18" should read — 18 —;
line 7, "24" should read — 24 —;
line 9, "24" should read — 24 —;
line 12, "18" should read — 18 —;
line 13, "as25)" should read — as 25) —;
line 14, "dinitrobenzyl)phosphorothioate24b" should read — dinitrobenzyl)phosphorothioate 24b —;
line 15, "23" should read — 23 —;
line 16, "19" should read — 19 —;
line 19, "24b" should read — 24b —;
line 21, "24c" should read — 24c —;
line 22, "23" should read — 23 —;
line 23, "21" should read — 21 —;
line 35, "30" should read — 30 —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 11, line 20, "27" should read -- 27 --;
line 27, "24a" should read -- 24a --, and "26" should read -- 26 --;
line 31, "27" should read -- 27 --;
line 33, "28a" should read -- 28a --;
line 37, "28a" should read -- 28a --;
line 42, "29" should read -- 29 --, and "FIG. 1a," should read -- FIG. 1a, --;
line 45, "24a" should read -- 24a --;
line 47, "31" should read -- 31 --;
line 48, "FIG. 1a," should read -- FIG. 1a, --;
line 52, "28" should read -- 28 --;
line 53, "internucieotide" should read -- internucleotide --;
line 59, "27" should read -- 27 --;
line 62, "24b" should read -- 24b --, and "26" should read -- 26 --;
line 63, "quahtity" should read -- quantity --;
line 64, "28b" should read -- 28b --;
Column 12, line 22, "27" should read -- 27 --;
line 24, "24e" should read -- 24c --, and "26" should read -- 26 --;
line 26, both instances of "28c" should read -- 28c --;
line 34, "29" should read -- 29 --;
line 36, "29" should read -- 29 --;
line 38, "30" should read -- 30 --;
line 43, "30" should read -- 30 --;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 13, line 38, "-35° C.," should read — -35°C, —;
          line 43, "intemucleotide" should read — internucleotide —;
          line 51, "32a" should read — 32a —;
          line 52, "33a" should read — 33a —;
          line 53, "34a" should read — 34a —;
          line 55, "22" should read — 22 —;
          line 56, "24c" should read — 24c —;
          line 58, "33a" should read — 33a —;
          line 59, "34a" should read — 34a —;
          line 63, "loc cit). 32b" should read — *loc cit*), 32b —;
          line 66, "32c" should read — 32c —;
          line 67, "33b and 33c" should read — 33b and 33c —;
Column 14, line 2, "34b and 34c" should read — 34b and 34c —;
          line 6, "33c" should read — 33c —;
          line 49, "24c and 34c" should read — 24c and 34c —;
          line 50, "38 and 39" should read — 38 and 39 —;
          line 54, "38 and 39" should read — 38 and 39 —;
          line 60, "34" should read — 34 —;
          line 62, "40" should read — 40 —;
Column 15, TABLE 1, lines 9-15, Compounds "23", "24c", "33a", "34a", "33b", "34b", "33c" and "34c" should read — 23 —, — 24c —, — 33a —, — 34a —, — 33b —, — 34b —, — 33c — and — 34c —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

```
Column 15, line 28, "29" should read -- 29 --;
           line 31, "28a" should read -- 28a --;
           line 33, "28c" should read -- 28c --;
           line 55, "buffer-acetonitril¢" should read
                   -- buffer-acetonitrile --;
           line 65, "18" should read -- 18 --;
Column 16, line 3, "50° C." should read -- 50°C --;
           line 9, "-80° C.)" should read -- -80°C) --;
           line 10, "16a" should read -- 16a --;
           line 20, "17a" should read -- 17a --;
           line 40, "18" should read -- 18 --;
           line 46, "19" should read -- 19 --;
           line 60, "60°-80° C.)" should read -- 60-80°C) --;
           line 61, "16b" should read -- 16b --;
Column 17, line 2, "16b" should read -- 16b --;
           line 9, "17b" should read -- 17b --;
           line 17, "ovemight" should read -- overnight --;
           line 23, "19" should read -- 19 --;
           line 25, "108°-109° C.;" should read -- 108-109°C; --;
           line 30, "21" should read -- 21 --;
           line 48, "21" should read -- 21 --;
           line 55, "23" should read -- 23 --;
           line 59, "-35° C." should read -- -35°C --;
Column 18, line 2, "cm3)" should read -- cm$^3$) --;
           line 10, "30°-40° C." should read -- 30-40°C --;
```

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 18, line 12, "23" should read — 23 —;
          line 23, "24a" should read — 24a —;
          line 26, "23" should read — 23 —;
          line 47, "30°-40° C.," should read — 30-40°C, —;
          line 49, "24a" should read — 24a —;
          line 60, "24b" should read — 24b —;
Column 19, line 14, "30°-40° C.," should read — 30-40°C, —;
          line 17, "24b" should read — 24b —;
          line 27, "24c" should read — 24c —;
          line 30, "23" should read — 23 —;
          line 44, "24c" should read — 24c —;
          line 48, "J3.6and" should read — $J$ 3.6 and —;
          line 49, "J3.0" should read — $J$ 3.0 —;
          line 50, "J6.1" should read — $J$ 6.1 —;
          line 55, "29. (a)" should read — 29 —;
          line 56, "A solution" should read — (a) A solution —;
          line 58, "24a" should read — 24a —;
          line 59, "loc cit. 26" should read — loc cit.) 26 —;
Column 20, line 17, "28a" should read — 28a —;
          line 25, "28a" should read — 28a —;
          line 30, "29" should read — 29 —;
          line 32, "24a" should read — 24a —;
          line 33, "31" should read — 31 —;
          line 42, "29" should read — 29 —;
          line 46, "24c" should read — 24c —;
          line 47, "26" should read — 26 —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 20, line 55, "28e" should read — 28c —;
           line 67, "30°-40°C.," should read — 30-40°C, —;
Column 21, line 2, "29" should read — 29 —;
           line 6, "31" should read — 31 —;
           line 8, "26" should read — 26 —;
           line 29, "31" should read — 31 —;
           line 40, "30" should read — 30 —;
           line 44, "29" should read — 29 —;
           line 45, "28c" should read — 28c —;
           line 66, "30" should read — 30 —;
Column 22, line 9, "33a" should read — 33a —;
           line 13, "23" should read — 23 —;
           line 17, "33a" should read — 33a —;
           line 24, "(11% s);" should read — (1 H, s); —;
           line 27, "34a" should read — 34a —;
           line 30, "thyroidinc" should read — thymidine —; and "24c" should read — 24c —;
           line 32, "33a" should read — 33a —;
           line 36, "34a" should read — 34a —;
           line 37, "$\delta_H H[(CD_3)_2SO]$" should read — $\delta_H[(CD_3)_2SO]$ —;
           line 40, "tt, m)," should read — H,m), —; and "8.5t" should read — 8.51 —;
           line 45, "33b" should read — 33b —;
           line 48, "thyroidinc" should read — thymidine —;
           line 49, "23" should read — 23 —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 22, line 54, "33b" should read — 33b —;
           line 63, "phenylxanthen-9-:yl)-2'-deoxycytidine" should read — phenylxanthen-9-yl)-2'-deoxycytidine —;
           line 65, "34b" should read — 34b —;
           line 67, "24c" should read — 24c —;
Column 23, line 3, "33b" should read — 33b —;
           line 6, "34b" should read — 34b —;
           line 17, "33c" should read — 33c —;
           line 22, "23" should read — 23 —;
           line 27, "33c" should read — 33c —;
           line 38, "34c" should read — 34c —;
           line 41, "24c" should read — 24c —;
           line 44, "33c" should read — 33c —;
           line 47, "34c" should read — 34c —;
Column 24, Claim 14, line 54, "claim 2" should read — claim 1 —;
           Claim 15, line 58, "claim 3" should read — claim 2 —;
           Claim 16, line 63, "claim 4" should read — claim 3 —;
           Claim 17, line 66, "claim 5" should read — claim 4 —;
Column 25, Claim 18, line 3, "claim 6" should read — claim 5 —;
           Claim 19, line 7, "claim 7" should read — claim 6 —;
           Claim 20, line 11, "claim 8" should read — claim 7 —;
           Claim 21, line 15, "claim 9" should read — claim 8 —;
Column 26, Claim 22, line 1, "claim 10" should read — claim 9 —; and
           Claim 23, line 5, "claim 11" should read — claim 10 —.

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above-identified patent and that said Letters Patent is hereby corrected as shown below:

The sheet of drawing, consisting of figures 1-4 should be deleted, to appear as per attached figures 1A-B. The drawing figure on the title page should be deleted.

This certificate supersedes Certificate of Correction issued December 29, 1998.

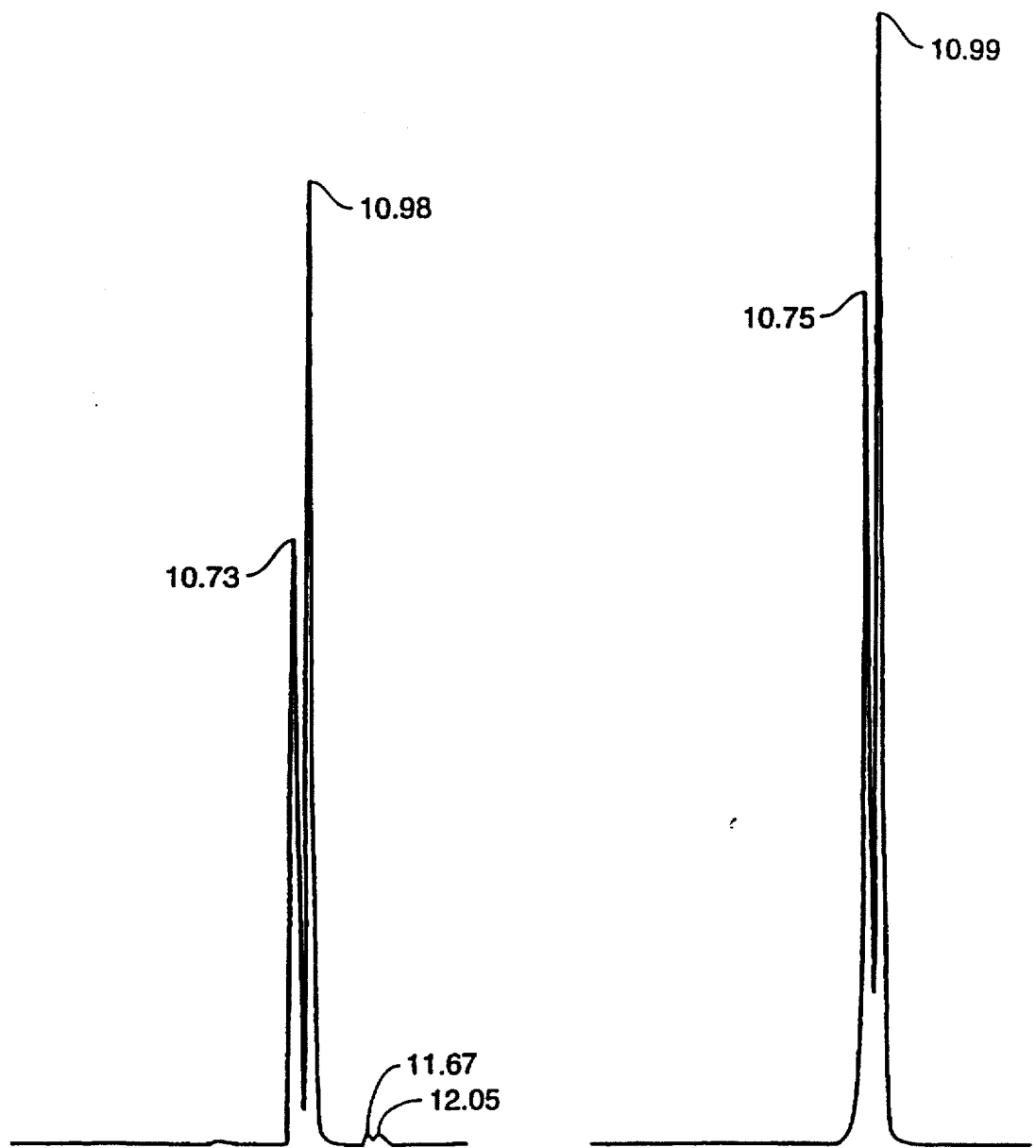
*FIG._1A*  *FIG._1B*

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above-identified patent and that said Letters Patent is hereby corrected as shown below:

Column 2, line 56, "et at," should read — et al. —;
           line 60, "quantifies" should read — quantities —;
           line 65, "couplirig" should read — coupling —;
Column 4, line 30, "2" should read — 2 —;
           line 32, "3" should read — 3 —;
           line 33, "4" should read — 4 —;
           line 34, "2" should read — 2 —;
           line 35, "2" should read — 2 —;
           line 36, "6" should read — 6 —;
           line 38, "6" should read — 6 —;
           line 39, "7" should read — 7 —;
           line 44, "3" should read — 3 —;
           line 45, "4" should read — 4 —;
           line 50, "Firsfly" should read — Firstly —;
           line 51, "2" should read — 2 —;
           line 54, "4" should read — 4 —;
Column 5, line 35, "a; X=S,$R^1R^2$=Cl" should read — a; X=S, $R^1=R^2$=Cl —;
           line 44, "8a" should read — 8a —;
           line 46, "8b" should read — 8b —;
           line 51, "p-thiocresoI," should read — p-thiocresol —;
           line 59, "8" should read — 8 —;
           line 62, "8b" should read — 8b —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 6, line 1, "Iaworska" should read — Jaworska —;
line 2, "8c" should read — 8c —;
line 5, "9" should read — 9 —;
line 13, "8d" should read — 8d —;
line 14, "Reese,." should read — Reese, —, and "Tel. Lett.," should read — Tet. Lett., —;
line 16, "8c" should read — 8c —, and "8" should read — 8 —;
line 17, "9" should read — 9 —;
line 33, "13" should read — 13 —;
line 34, "14" should read — 14 —;
line 37, "199.0)" should read — 1990) —;
line 38, "10" should read — 10 —;
line 39, "13" should read — 13 —;
line 41, "11" should read — 11 —;
line 43, "12" should read — 12 —;
line 45, "14" should read — 14 —;
line 47, "13" should read — 13 —;
line 52, both instances of "13" should read — 13 —;
line 61, "13 or 14" should read — 13 or 14 —;
line 62, "17a, 17b" should read — 17a, 17b —;
line 63, "20" should read — 20 —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 7, line 44, "50° C.," should read — 50°C, —;
 line 45, 0° C.," should read — 0°C, —;
 line 51, "17a and 17b," should read — 17a and 17b, —;
 line 53, "15a" should read — 15a —;
 line 54, "50° C.," should read — 50°C, —;
 line 55, "16a" should read — 16a —;
 line 56, "16a" should read — 16a —;
 line 57, "17a" should read — 17a —;
 line 59, "17b" should read — 17b —;
 line 62, "15b" should read — 15b —;
 line 63, "18" should read — 18 —;
Column 8, line 3, "17a" should read — 17a —;
 line 5, "17b" should read — 17b —;
 line 6, "13" should read — 13 —;
 line 7, "14" should read — 14 —;
 line 8, "19" should read — 19 —;
 line 12, "17b" should read — 17b —;
 line 14, "20" should read — 20 —;
 line 19, "21" should read — 21 —;
Column 9, line 16, "-35° C.," should read — -35°C, —, and "24a:" should read — 24a: —;
 line 17, "18" should read — 18 —, and "24b: 19" should read — 24b: 19 —;
 line 18, "24c: 21" should read — 24c: 21 —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 9, line 19, "4-methylmoxpholine" should read
— 4-methylmorpholine —; and "Et NH⁺ HCO₃—." should read — Et₃NH⁺ HCO₃⁻. —;
line 21, "22" should read — 22 —;
line 24, "24a, 24b and 24c" should read — 24a, 24b and 24c —;
line 25, "22" should read — 22 —;
line 26, "from-phosphorous" should read
— from phosphorous —;
line 28, "-35° C.," should read — -35°C, —;
line 32, "23" should read — 23 —;
line 34, "23" should read — 23 —;

Column 10, line 1, "23" should read — 23 —;
line 2, "18" should read — 18 —;
line 7, "24" should read — 24 —;
line 9, "24" should read — 24 —;
line 12, "18" should read — 18 —;
line 13, "as25)" should read — as 25) —;
line 14, "dinitrobenzyl)phosphorothioate24b" should read — dinitrobenzyl)phosphorothioate 24b —;
line 15, "23" should read — 23 —;
line 16, "19" should read — 19 —;
line 19, "24b" should read — 24b —;
line 21, "24c" should read — 24c —;
line 22, "23" should read — 23 —;
line 23, "21" should read — 21 —;
line 35, "30" should read — 30 —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 11, line 20, "27" should read — 27 —;
          line 27, "24a" should read — 24a —, and "26" should read — 26 —;
          line 31, "27" should read — 27 —;
          line 33, "28a" should read — 28a —;
          line 37, "28a" should read — 28a —;
          line 42, "29" should read — 29 —, and "FIG. 1a," should read — FIG. 1a, —;
          line 45, "24a" should read — 24a —;
          line 47, "31" should read — 31 —;
          line 48, "FIG. 1a," should read — FIG. 1a, —;
          line 52, "28" should read — 28 —;
          line 53, "internucieotide" should read — internucleotide —;
          line 59, "27" should read — 27 —;
          line 62, "24b" should read — 24b —, and "26" should read — 26 —;
          line 63, "quahtity" should read — quantity —;
          line 64, "28b" should read — 28b —;
Column 12, line 22, "27" should read — 27 —;
          line 24, "24e" should read — 24c —, and "26" should read — 26 —;
          line 26, both instances of "28c" should read — 28c —;
          line 34, "29" should read — 29 —;
          line 36, "29" should read — 29 —;
          line 38, "30" should read — 30 —;
          line 43, "30" should read — 30 —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 13, line 38, "-35° C.," should read — -35°C, —;
    line 43, "intemucleotide" should read
    — internucleotide —;
    line 51, "32a" should read — 32a —;
    line 52, "33a" should read — 33a —;
    line 53, "34a" should read — 34a —;
    line 55, "22" should read — 22 —;
    line 56, "24c" should read — 24c —;
    line 58, "33a" should read — 33a —;
    line 59, "34a" should read — 34a —;
    line 63, "loc cit). 32b" should read — <u>loc cit</u>), 32b —;
    line 66, "32c" should read — 32c —;
    line 67, "33b and 33c" should read — 33b and 33c —;
Column 14, line 2, "34b and 34c" should read — 34b and 34c —;
    line 6, "33c" should read — 33c —;
    line 49, "24c and 34c" should read — 24c and 34c —;
    line 50, "38 and 39" should read — 38 and 39 —;
    line 54, "38 and 39" should read — 38 and 39 —;
    line 60, "34" should read — 34 —;
    line 62, "40" should read — 40 —;
Column 15, TABLE 1, lines 9-15, Compounds "23", "24c", "33a", "34a", "33b", "34b", "33c" and "34c" should read
    — 23 —, — 24c —, — 33a —, — 34a —, — 33b —, — 34b —, — 33c — and — 34c —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 15, line 28, "29" should read — 29 —;
            line 31, "28a" should read — 28a —;
            line 33, "28c" should read — 28c —;
            line 55, "buffer-acetonitrilɇ" should read — buffer-acetonitrile —;
            line 65, "18" should read — 18 —;
Column 16, line 3, "50° C." should read — 50°C —;
            line 9, "-80° C.)" should read — -80°C) —;
            line 10, "16a" should read — 16a —;
            line 20, "17a" should read — 17a —;
            line 40, "18" should read — 18 —;
            line 46, "19" should read — 19 —;
            line 60, "60°-80° C.)" should read — 60-80°C) —;
            line 61, "16b" should read — 16b —;
Column 17, line 2, "16b" should read — 16b —;
            line 9, "17b" should read — 17b —;
            line 17, "ovemight" should read — overnight —;
            line 23, "19" should read — 19 —;
            line 25, "108°-109° C.;" should read — 108-109°C; —;
            line 30, "21" should read — 21 —;
            line 48, "21" should read — 21 —;
            line 55, "23" should read — 23 —;
            line 59, "-35° C." should read — -35°C —;
Column 18, line 2, "cm3)" should read — $cm^3$) —;
            line 10, "30°-40° C." should read — 30-40°C —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

```
Column 18, line 12, "23" should read — 23 —;
           line 23, "24a" should read — 24a —;
           line 26, "23" should read — 23 —;
           line 47, "30°-40° C.," should read — 30-40°C, —;
           line 49, "24a" should read — 24a —;
           line 60, "24b" should read — 24b —;
Column 19, line 14, "30°-40° C.," should read — 30-40°C, —;
           line 17, "24b" should read — 24b —;
           line 27, "24c" should read — 24c —;
           line 30, "23" should read — 23 —;
           line 44, "24c" should read — 24c —;
           line 48, "J3.6and" should read — J 3.6 and —;
           line 49, "J3.0" should read — J 3.0 —;
           line 50, "J6.1" should read — J 6.1 —;
           line 55, "29. (a)" should read — 29 —;
           line 56, "A solution" should read — (a) A solution —;
           line 58, "24a" should read — 24a —;
           line 59, "loc cit. 26" should read — loc cit.) 26 —;
Column 20, line 17, "28a" should read — 28a —;
           line 25, "28a" should read — 28a —;
           line 30, "29" should read — 29 —;
           line 32, "24a" should read — 24a —;
           line 33, "31" should read — 31 —;
           line 42, "29" should read — 29 —;
           line 46, "24c" should read — 24c —;
           line 47, "26" should read — 26 —;
```

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above—identified patent and that said Letters Patent is hereby corrected as shown below:

Column 20, line 55, "28e" should read — 28c —;
line 67, "30°-40°C.," should read — 30-40°C, —;
Column 21, line 2, "29" should read — 29 —;
line 6, "31" should read — 31 —;
line 8, "26" should read — 26 —;
line 29, "31" should read — 31 —;
line 40, "30" should read — 30 —;
line 44, "29" should read — 29 —;
line 45, "28c" should read — 28c —;
line 66, "30" should read — 30 —;
Column 22, line 9, "33a" should read — 33a —;
line 13, "23" should read — 23 —;
line 17, "33a" should read — 33a —;
line 24, "(11% s);" should read — (1 H, s); —;
line 27, "34a" should read — 34a —;
line 30, "thyroidinc" should read — thymidine —; and "24c" should read — 24c —;
line 32, "33a" should read — 33a —;
line 36, "34a" should read — 34a —;
line 37, "$\delta_H H[(CD_3)_2SO]$" should read — $\delta_H[(CD_3)_2SO]$ —;
line 40, "tt, m)," should read — H,m), —; and "8.5t" should read — 8.51 —;
line 45, "33b" should read — 33b —;
line 48, "thyroidinc" should read — thymidine —;
line 49, "23" should read — 23 —;

UNITED STATES PATENT AND TRADEMARK OFFICE
CERTIFICATE OF CORRECTION

PATENT NO. : 5,708,161
DATED : January 13, 1998
INVENTOR(S) : Colin Bernard Reese It is certified that error appears in the above-identified patent and that said Letters Patent is hereby corrected as shown below:

Column 22, line 54, "33b" should read — 33b —;
line 63, "phenylxanthen-9-:yl)-2'-deoxycytidine" should read — phenylxanthen-9-yl)-2'-deoxycytidine —;
line 65, "34b" should read — 34b —;
line 67, "24c" should read — 24c —;
Column 23, line 3, "33b" should read — 33b —;
line 6, "34b" should read — 34b —;
line 17, "33c" should read — 33c —;
line 22, "23" should read — 23 —;
line 27, "33c" should read — 33c —;
line 38, "34c" should read — 34c —;
line 41, "24c" should read — 24c —;
line 44, "33c" should read — 33c —;
line 47, "34c" should read — 34c —;
Column 24, Claim 14, line 54, "claim 2" should read — claim 1 —;
Claim 15, line 58, "claim 3" should read — claim 2 —;
Claim 16, line 63, "claim 4" should read — claim 3 —;
Claim 17, line 66, "claim 5" should read — claim 4 —;
Column 25, Claim 18, line 3, "claim 6" should read — claim 5 —;
Claim 19, line 7, "claim 7" should read — claim 6 —;
Claim 20, line 11, "claim 8" should read — claim 7 —;
Claim 21, line 15, "claim 9" should read — claim 8 —;
Column 26, Claim 22, line 1, "claim 10" should read — claim 9 —; and
Claim 23, line 5, "claim 11" should read — claim 10 —.

Signed and Sealed this

Twentieth Day of April, 1999

Attest:

Q. TODD DICKINSON

Attesting Officer

Acting Commissioner of Patents and Trademarks